United States Patent
Abbott et al.

(10) Patent No.: US 12,168,026 B2
(45) Date of Patent: Dec. 17, 2024

(54) METHODS AND COMPOSITIONS FOR WOUND HEALING

(71) Applicants: Nicholas L. Abbott, Madison, WI (US); Jonathan F. McAnulty, Oregon, WI (US)

(72) Inventors: Nicholas L. Abbott, Madison, WI (US); Jonathan F. McAnulty, Oregon, WI (US)

( * ) Notice: Subject to any disclaimer, the term of this patent is extended or adjusted under 35 U.S.C. 154(b) by 0 days.

(21) Appl. No.: 18/376,044

(22) Filed: Oct. 3, 2023

(65) Prior Publication Data

US 2024/0139237 A1     May 2, 2024

Related U.S. Application Data

(63) Continuation of application No. 17/268,622, filed as application No. PCT/US2019/046831 on Aug. 16, 2019, now Pat. No. 11,793,832.

(Continued)

(51) Int. Cl.
| | |
|---|---|
| *A61K 33/38* | (2006.01) |
| *A61K 9/70* | (2006.01) |
| *A61K 31/167* | (2006.01) |
| *A61K 31/381* | (2006.01) |
| *A61K 31/445* | (2006.01) |
| *A61K 33/24* | (2019.01) |
| *A61K 47/32* | (2006.01) |
| *A61K 47/34* | (2017.01) |
| *A61K 47/36* | (2006.01) |

(Continued)

(52) U.S. Cl.
CPC ........... *A61K 33/38* (2013.01); *A61K 9/7092* (2013.01); *A61K 31/167* (2013.01); *A61K 31/381* (2013.01); *A61K 31/445* (2013.01); *A61K 33/24* (2013.01); *A61K 47/32* (2013.01); *A61K 47/34* (2013.01); *A61K 47/36* (2013.01); *A61K 47/38* (2013.01); *A61L 15/28* (2013.01); *A61L 15/44* (2013.01); *A61P 17/02* (2018.01); *A61P 31/02* (2018.01); *A61L 2300/404* (2013.01); *A61L 2300/61* (2013.01)

(58) Field of Classification Search
None
See application file for complete search history.

(56) References Cited

U.S. PATENT DOCUMENTS

| | | | |
|---|---|---|---|
| 11,793,832 B2 * | 10/2023 | Abbott | A61K 31/167 |
| 2004/0153040 A1 | 8/2004 | Martineau et al. | |
| 2015/0283287 A1 | 10/2015 | Agarwal et al. | |

FOREIGN PATENT DOCUMENTS

| | | |
|---|---|---|
| WO | WO 2009/097508 | 8/2009 |
| WO | WO 2011/100425 | 8/2011 |

(Continued)

OTHER PUBLICATIONS

Herron, M., et al., Interfacial Stacks of Polymeric Nanofilms on Soft Biological Surfaces that Release Multiple Agents, ACS Appl. Mater. Interfaces, 8 (2016) pp. 26541-26551. (Year: 2016).*

(Continued)

*Primary Examiner* — Dominic Lazaro
(74) *Attorney, Agent, or Firm* — CASIMIR JONES, S.C.; J. Mitchell Jones

(57) ABSTRACT

The present invention relates to large scale manufacture of nanoscale microsheets for use in applications such as wound healing or modification of a biological or medical surface.

15 Claims, 6 Drawing Sheets

Related U.S. Application Data

(60) Provisional application No. 62/718,988, filed on Aug. 16, 2018.

(51) Int. Cl.
    *A61K 47/38*     (2006.01)
    *A61L 15/28*     (2006.01)
    *A61L 15/44*     (2006.01)
    *A61P 17/02*     (2006.01)
    *A61P 31/02*     (2006.01)

(56) References Cited

FOREIGN PATENT DOCUMENTS

| WO | WO 2014/074503 | 5/2014 |
|----|----------------|--------|
| WO | WO 2018/023021 | 2/2018 |

OTHER PUBLICATIONS

International Search Report and Written Opinion for PCT/US2019/046831. Mailed Oct. 21, 2019. 7 pages.

Agarwal et al., Surfaces modified with nanometer-thick silver-impregnated polymeric films that kill bacteria but support growth of mammalian cells. Biomaterials. Feb. 2010;31(4):680-90.

Ariga et al., Ultrathin films of inorganic materials (SiO2 nanoparticle, montmorillonite microplate, and molybdenum oxide) prepared by alternate layer-by-layer assembly with organic polyions. Appl. Clay Sci. 1999, 15:137-152.

Cai et al., Comparison of toxicity effects of ropivacaine, bupivacaine, and lidocaine on rabbit intervertebral disc cells in vitro. Spine J. Mar. 1, 2014;14(3):483-90.

Caruso et al., 2. Assembly of Alternating Polyelectrolyte and Protein Multilayer Films for Immunosensing. Langmuir, 1997, 13, 13, 3427-3433.

Caruso et al., Preparation and Characterization of Ordered Nanoparticle and Polymer Composite Multilayers on Colloids. Langmuir. 1999, 15, 23, 8276-8281.

Caruso et al., Protein Multilayer Formation on Colloids through a Stepwise Self-Assembly Technique. J. Am. Chem. Soc. 1999, 121, 25, 6039-6046.

Cassagneau et al., Layer-by-Layer Assembly of Thin Film Zener Diodes from Conducting Polymers and CdSe Nanoparticles. J. Am. Chem. Soc. 1998, 120, 7848-7859.

Decher et al., Buildup of ultrathin multilayer films by a self-assembly process: III. Consecutively alternating adsorption of anionic and cationic polyelectrolytes on charged surfaces. Thin Solid Films. 1992, vol. 210-211, Part 2, 831-835.

Decher. Fuzzy Nanoassemblies: Toward Layered Polymeric Multicomposites. Science. 1997, 277(5330) 1232-1237.

Dere et al., The comparison of the effects of different doses of levobupivacaine infiltration on wound healing. J Invest Surg. Mar.-Apr. 2009;22(2):112-6.

Gribskov et al., Sequence Analysis Primer, Stockton Press, 1991. TOC only. 13 pages.

Haas et al., Ketamine: a review of its pharmacologic properties and use in ambulatory anesthesia. Anesth Prog. 1992;39(3):61-8.

Hanci et al., Comparison of the effects of bupivacaine, lidocaine, and tramadol infiltration on wound healing in rats. Rev Bras Anestesiol. Nov.-Dec. 2012;62(6):799-810.

Herron et al., Gallium-Loaded Dissolvable Microfilm Constructs that Provide Sustained Release of Ga(3+) for Management of Biofilms. Adv Healthc Mater. Dec. 30, 2015;4(18):2849-59.

Herron et al., Interfacial Stacks of Polymeric Nanofilms on Soft Biological Surfaces that Release Multiple Agents. ACS Appl Mater Interfaces. Oct. 12, 2016;8(40):26541-26551.

Herron et al., Reduction in wound bioburden using a silver-loaded dissolvable microfilm construct. Adv Healthc Mater. Jun. 2014;3(6):916-28.

Joanny. Polyelectrolyte adsorption and charge inversion. Eur. Phys. J. Biol. 1999, 9(1):117-122.

Johnson et al., Local anesthetics as antimicrobial agents: a review. Surg Infect (Larchmt). Apr. 2008;9(2):205-13.

Keller et al., Layer-by-Layer Assembly of Intercalation Compounds and Heterostructures on Surfaces: Toward Molecular "Beaker" Epitaxy. J. Am. Chem. Soc. 1994, 116, 19, 8817-8818.

Ladam et al., In Situ Determination of the Structural Properties of Initially Deposited Polyelectrolyte Multilayers. Langmuir, 2000, 16, 3, 1249-1255.

Luo et al., Antibacterial effect of dressings containing multivalent silver ion carried by zirconium phosphate on experimental rat burn wounds. Wound Repair Regen. Nov.-Dec.2008;16(6):800-4.

Lvov et al., Alternate Assembly of Ordered Multilayers of SiO2 and Other Nanoparticles and Polyions. Langmuir, 1997, 13, 23, 6195-6203.

Lvov et al., Assembly of Multicomponent Protein Films by Means of Electrostatic Layer-by-Layer Adsorption. J. Am. Chem. Soc. 1995, 117, 22, 6117-6123.

\* cited by examiner

METHODS AND COMPOSITIONS FOR WOUND HEALING

CROSS-REFERENCE TO RELATED APPLICATIONS

This application is a continuation of U.S. patent application Ser. No. 17/268,622, filed Feb. 16, 2021, now allowed, which is a U.S National Stage Application of International Patent Application No. PCT/US2019/046831, filed Aug. 16, 2019, which claims priority to U.S. Provisional Patent Application No. 62/718,988 filed Aug. 16, 2018, the contents of each of which are incorporated by reference in their entirety.

FIELD OF THE INVENTION

The present invention relates to large scale manufacture of nanoscale microsheets for use in applications such as wound healing or modification of a biological or medical surface.

BACKGROUND OF THE INVENTION

Chronic wound care often involves management of bacterial loading as well as pain management. For non-opioid pain management, local anesthetics administered via injection (1.25-5 mg mL$^{-1}$), such as bupivacaine (Bp), are commonly used.[1] Compared to other anesthetic agents (e.g. lidocaine), Bp is preferable due to its longer duration of action.[2] However, bupivacaine administered at local incisions of rats wounds at concentration of 5 mg mL$^{-1}$ has been reported to decrease collagen production as well as cause significant inflammation,[3] indicating that the need for strategies for controlled dosage of anesthetic agents at wound sites. Similarly, topical antimicrobial treatment (i.e. a silver dressing containing a high loadings of silver) has been reported to cause delayed wound healing, again demonstrating the need for platforms that provide the controlled delivery of silver.

SUMMARY OF THE INVENTION

The present invention relates to large scale manufacture of nanoscale microsheets for use in applications such as wound healing or modification of a biological or medical surface.

In some embodiments, the present invention provides devices for application to a wound comprising: a first polymer layer comprising a first bioactive agent; a second polymer layer comprising a second bioactive agent; and a third polymer layer positioned in between the first and second polymer layer so that the three polymer layers are stacked in a sandwich-type structure.

In some preferred embodiments, the first polymer layer is a nanoscale polymer multilayer. In some preferred embodiments, the nanoscale polymer multilayer comprises alternating layers of at least one positively charged polyelectrolyte and at least one negatively charged polyelectrolyte. In some preferred embodiments, the at least one positively charged polyelectrolyte is selected form the group consisting of poly(allylamine hydrochloride) (PAH), polyl-lysine (PLL), poly(ethylene imine) (PEI), poly(histidine), poly(N,N-dimethyl aminoacrylate), poly(N,N,N-trimethylaminoacrylate chloride), poly(methyacrylamidopropyltrimethyl ammonium chloride), and natural or synthetic polysaccharides such as chitosan. In some preferred embodiments, the at least one negatively charged polyelectrolyte is selected from the group consisting of poly(acrylic acid) (PAA), poly(styrenesulfonate) (PSS), alginate, hyaluronic acid, heparin, heparan sulfate, chondroitin sulfate, dextran sulfate, poly(methacrylic acid), oxidized cellulose, carboxymethyl cellulose, polyaspartic acid, and polyglutamic acid.

In some preferred embodiments, the first bioactive agent is an antimicrobial agent selected from the groups consisting of small molecule antimicrobial agents, charged small molecule antimicrobial agents, antimicrobial polypeptides, metallic particles, and bioactive metal ions. In some preferred embodiments, the bioactive metal ion is a metal ion antimicrobial agent. In some preferred embodiments, the metal ion antimicrobial agent is a metal ion, metal ion salt, or metal ion nanoparticle. In some preferred embodiments, the metal ion antimicrobial agent is a silver ion, silver salt, or silver nanoparticle. In some preferred embodiments, the bioactive metal ion is a metal ion antibiofilm agent. In some preferred embodiments, the metal ion antibiofilm agent is a metal ion, metal ion salt, or metal ion nanoparticle. In some preferred embodiments, the metal ion antibiofilm agent is a gallium ion, galium salt, or gallium nanoparticle. In some preferred embodiments, the small molecule antimicrobial agent is selected from the group consisting of chlorhexidine, an antibiotic, polyhexamethylene biguanide (PHMB), iodine, cadexomer iodine, and povidone iodine (PVI).

In some preferred embodiments, the second polymer layer is a water soluble microscale polymer layer. In some preferred embodiments, the water soluble microscale polymer layer is selected from the group consisting of polyvinyl alcohol (PVA), polyacrylic acid (PAA), polyvinylpyrrolidone (PVP), carboxymethyl cellulose (CMC), sodium carboxymethyl cellulose, methylcellulose, ethylcellulose, ethylmethyl cellulose, hydroxyethyl cellulose (HEC), hydroxylpropyl cellulose (HPC), hydroxypropyl methylcellulose (HPMC), alginates, polyvinylacetate (PVAc), polylactic acid (PLA), polylactic-co-glycolic acid (PLGA), polyglycolic acid, and polyanhydrides. In some preferred embodiments, the water soluble microscale polymer layer is PVA. In some preferred embodiments, the second bioactive agent is an analgesic agent selected from the group consisting of acetaminophen, anileridine, acetylsalicylic acid, buprenorphine, butorphanol, fentanyl, fentanyl citrate, codeine, rofecoxib, hydrocodone, hydromorphone, hydromorphone hydrochloride, levorphanol, alfentanil hydrochloride, meperidine, meperidine hydrochloride, methadone, morphine, nalbuphine, opium, levomethadyl, hyaluronate sodium, sufentanil citrate, capsaicin, tramadol, leflunomide, oxycodone, oxymorphone, celecoxib, pentazocine, propoxyphene, benzocaine, lidocaine, dezocine, clonidine, butalbital, phenobarbital, tetracaine, phenazopyridine, sulfamethoxazole/phenazopyridine, sulfisoxazole/phenazopyridine, amylocaine, ambucaine, articaine, benzocaine, benzonatate, bupivacaine, butacaine, butanilicaine, chloroprocaine, cinchocaine, cyclomehtycaine, dibucaine, diperodon, dimethisoquin, dimethocaine, eucaine, etidocaine, hexylcaine, fomocaine, fotocaine, hydroxyprocaine, isobucaine, levobupivicaine, iodocaine, mepivacaine, meprylcaine, metabutoxycaine, nitracaine, orthocaine, oxetacaine, oxybuprocaine, paraethocycaine, phenacaine, piperocaine, piridocaine, pramocaine, prilocaine, primacaine, procaine, procainamide, proparacaine, propoxycaine, pyrrocaine, quinisocaine, ropivacaine, trimecaine, tetracaine, tolycaine, and tropacocaine. In some preferred embodiments, the analgesic agent is a local anasthetic selected from the group consisting of bupivacaine, lidocaine, articaine, prilocaine, and mepivacaine.

In some preferred embodiments, the third polymer layer is a water soluble microscale polymer layer. In some preferred embodiments, the water soluble microscale polymer layer is polyvinylpyrrolidone (PVP), carboxymethyl cellulose (CMC), sodium carboxymethyl cellulose, methylcellulose, ethylcellulose, ethylmethyl cellulose, hydroxyethyl cellulose (HEC), hydroxylpropyl cellulose (HPC), hydroxypropyl methylcellulose (HPMC), alginates, polyvinylacetate (PVAc), polylactic acid (PLA), polylactic-co-glycolic acid (PLGA), polyglycolic acid, and polyanhydrides. In some preferred embodiments, the water soluble microscale polymer layer is formed from a different polymer than the second polymer layer. In some preferred embodiments, the third water soluble microscale polymer layer is PLGA. In some preferred embodiments, the third polymer layer does not comprise a bioactive agent. In some preferred embodiments, the third polymer layer modulates diffusion of the second bioactive agent towards the wound bed. In some preferred embodiments, the third polymer layer has a thickness of from 10 to 100 μm, and more preferably from 20-40 μm.

In some preferred embodiments, the devices further comprise a fourth polymer layer positioned beneath the first polymer layer in the sandwich-type structure. In some preferred embodiments, the fourth polymer layer is a water soluble microscale polymer layer. In some preferred embodiments, the water soluble microscale polymer layer is selected from the group consisting of polyvinyl alcohol (PVA), polyacrylic acid (PAA), polyvinylpyrrolidone (PVP), carboxymethyl cellulose (CMC), sodium carboxymethyl cellulose, methylcellulose, ethylcellulose, ethylmethyl cellulose, hydroxyethyl cellulose (HEC), hydroxylpropyl cellulose (HPC), hydroxypropyl methylcellulose (HPMC), alginates, polyvinylacetate (PVAc), polylactic acid (PLA), polylactic-co-glycolic acid (PLGA), polyglycolic acid, and polyanhydrides. In some preferred embodiments, the water soluble microscale polymer layer is PVA. In some preferred embodiments, the fourth polymer layer comprises an analgesic agent selected from the group consisting of acetaminophen, anileridine, acetylsalicylic acid, buprenorphine, butorphanol, fentanyl, fentanyl citrate, codeine, rofecoxib, hydrocodone, hydromorphone, hydromorphone hydrochloride, levorphanol, alfentanil hydrochloride, meperidine, meperidine hydrochloride, methadone, morphine, nalbuphine, opium, levomethadyl, hyaluronate sodium, sufentanil citrate, capsaicin, tramadol, leflunomide, oxycodone, oxymorphone, celecoxib, pentazocine, propoxyphene, benzocaine, lidocaine, dezocine, clonidine, butalbital, phenobarbital, tetracaine, phenazopyridine, sulfamethoxazole/phenazopyridine, sulfisoxazole/phenazopyridine, amylocaine, ambucaine, articaine, benzocaine, benzonatate, bupivacaine, butacaine, butanilicaine, chloroprocaine, cinchocaine, cyclomehtycaine, dibucaine, diperodon, dimethisoquin, dimethocaine, eucaine, etidocaine, hexylcaine, fomocaine, fotocaine, hydroxyprocaine, isobucaine, levobupivicaine, iodocaine, mepivacaine, meprylcaine, metabutoxycaine, nitracaine, orthocaine, oxetacaine, oxybuprocaine, paraethocycaine, phenacaine, piperocaine, piridocaine, pramocaine, prilocaine, primacaine, procaine, procainamide, proparacaine, propoxycaine, pyrrocaine, quinisocaine, ropivacaine, trimecaine, tetracaine, tolycaine, and tropacocaine. In some preferred embodiments, the analgesic agent is a local anasthetic selected from the group consisting of bupivacaine, lidocaine, articaine, prilocaine, and mepivacaine.

In some preferred embodiments, the devices further comprise a fifth polymer layer positioned above the second polymer layer in the sandwich-type structure. In some preferred embodiments, the fifth polymer layer is a water soluble microscale polymer layer. In some preferred embodiments, the water soluble microscale polymer layer is selected from the group consisting of polyvinyl alcohol (PVA), polyacrylic acid (PAA), polyvinylpyrrolidone (PVP), carboxymethyl cellulose (CMC), sodium carboxymethyl cellulose, methylcellulose, ethylcellulose, ethylmethyl cellulose, hydroxyethyl cellulose (HEC), hydroxylpropyl cellulose (HPC), hydroxypropyl methylcellulose (HPMC), alginates, polyvinylacetate (PVAc), polylactic acid (PLA), polylactic-co-glycolic acid (PLGA), polyglycolic acid, and polyanhydrides. In some preferred embodiments, the water soluble microscale polymer layer is PLGA. In some preferred embodiments, the fifth polymer layer does not comprise a bioactive agent. In some preferred embodiments, the fifth polymer layer acts a barrier to direct the release of the first and second bioactive agents towards the wound bed. In some preferred embodiments, the fifth polymer layer has a thickness of from 100 to 200 μm, more preferably from 120-130 μm.

In some preferred embodiments, the present invention provides methods of treating a wound comprising applying a device as described above to the surface of wound.

In some preferred embodiments, the present invention provides a device as described above for treating a wound or enhancing the healing of a wound.

BRIEF DESCRIPTION OF THE DRAWINGS

FIG. 4. a) Cytotoxicity of solutions of Bp or $Ag^+$ ions toward NIH 3T3 mouse fibroblast cells. The figure shows the percentage of fibroblasts remaining viable (measured by mitochondrial dehydrogenase activity) following 24 h-treatment with solutions of $Ag^+$ ions (from reference[6]) or Bp. b) CFU (per mL) of bacterial suspension of *P. aeruginosa* (ATCC 27853) that contains either no agents, Bp (0.6 mg $mL^{-1}$), $Ag^+$ ($AgNO_3$: 0.3 or 0.4 μg $mL^{-1}$), or mixture of Bp and $Ag^+$ following 24-h incubation. Data are presented as mean±standard of error (n>3).

FIG. 5. a) Release of Bp from a PVA film (loadings of Bp: 0.2, 0.4, 0.9, 1.8 μg $cm^{-2}$) into PBS. b) Release of Bp from a PVA microfilm with and without a PLGA cap; the thickness of the PLGA cap was changed by varying the concentration of PLGA in the casting solution used to make the PLGA film (1%, 1.75%, or 5%).

FIG. 6. Release of Bp from a microfilm construct containing two PVA films (each loaded with 0.9 mg $cm^{-2}$ of Bp) that were separated by PLGA film (made from solution containing 1.75% PLGA). A rapid dissolution of the top PVA layer provides a burst release of Bp (within 5 minutes).

Following the burst release of Bp, a sustained release of Bp was delivered from the bottom, PLGA-capped layers.

FIG. 7. Unidirectional burst release of Bp from a composite film onto wound surface and its effect toward wound healing. a) Schematic of a Bp-loaded PVA film (0.9 μg $cm^{-2}$ Bp) that was capped with a PLGA barrier layer (PLGA film made from solution of 5% PLGA) before and after the structure was flipped as well as the release profile of Bp from the structures. Minimal Bp was released through the top PLGA barrier layer. Bp, however, was released from the bottom side of the platform (of the flipped structures) within minutes. b) Representative photographs of wounds on post-operative days 0, 10, and 14 in wounds that receive composite PVA/PLGA film containing no Bp and film containing 1.8 mg $cm^{-2}$. c) Percentage of original wound size on post-operative days 3, 6, 10, 12, and 14 in wounds that did not receive treatment, wounds that were treated with films containing no Bp, and wounds treated with films containing 0.9 and 1.8 mg $cm^{-2}$.

FIG. 8. Unidirectional sustained release of both Ag and Bp. a) Schematic of microfilm composite (namely structure (a)) consisting of Bp-loaded PVA MF (Bp loading of 0.45 mg $cm^{-2}$), AgNPs-loaded PEMs (Ag loading of 10 μg $cm^{-2}$), thin PLGA MF, Bp-loaded PVA MF (Bp loading of 0.45 mg $cm^{-2}$), and PLGA sealant (listed from the bottom to the top layer) as well as its flipped structure. b) Release of Bp (left axis) and Ag (right axis) from structure (a) and its flipped structure. Only a small amount of both Ag and Bp can be released through the top PLGA sealant. In contrast, both agents were able to be released from the bottom side of the film (as characterized from the flipped structure).

FIG. 9. Number of CFU of *P. aeruginosa* within bacterial suspension over PDMS sheet coated with composite microfilms containing Bp and AgNPs following exposure of the PDMS sheet to three fresh bacterial inoculum over a 3-day period (first incubation over 0-24 h, second over 24-48 h, and third over 48-72 h). The PDMS sheet was rinsed between each incubation period. Error bars show standard of deviation (n=3).

DEFINITIONS

To facilitate an understanding of the invention set forth in the disclosure that follows, a number of terms are defined below.

The term "wound" refers broadly to injuries to the skin and subcutaneous tissue initiated in different ways (e.g., pressure sores from extended bed rest and wounds induced by trauma) and with varying characteristics. The methods and compositions described herein are useful for treatment of all types of wounds, including wounds to internal and external tissues, and wounds induced during medical procedures (e.g., surgical procedures) (e.g., abdominal surgery, hernia surgery, gastrointestinal surgery, bariatric surgery, reconstruction surgery, dural membrane surgery, etc). Wounds may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum).

The term "partial thickness wound" refers to wounds that encompass Grades I-III; examples of partial thickness wounds include burn wounds, pressure sores, venous stasis ulcers, and diabetic ulcers. The term "deep wound" is meant to include both Grade III and Grade IV wounds. The present invention contemplates treating all wound types, including deep wounds and chronic wounds.

The term "chronic wound" refers to a wound that has not healed within 30 days.

The phrases "promote wound healing," "enhance wound healing," and the like refer to either the induction of the formation of granulation tissue of wound contraction and/or the induction of epithelialization (i.e., the generation of new cells in the epithelium). Wound healing is conveniently measured by decreasing wound area.

The term "bioactive agent" refers to known or potential chemical compounds that induce a desired pharmacological, physiological effect useful in the treatment and healing of a wound, wherein the effect may be prophylactic or therapeutic. The terms also encompass pharmaceutically acceptable, pharmacologically active derivatives of those active agents specifically mentioned herein, including, but not limited to, trophic factors, extracellular matrices, enzymes, enzyme inhibitors, defensins, polypeptides, anti-infective agents (including but not limited to ionic silver, elemental silver, and silver nanoparticles), buffering agents, vitamins and minerals, analgesics, anticoagulants, coagulation factors, anti-inflammatory agents, vasoconstrictors, vasodilators, diuretics, and anti-cancer agents.

The term "polymer multilayer" refers to the composition formed by sequential and repeated application of polymer(s) to form a multilayered structure. For example, polyelectrolyte multilayers are polymer multilayers are formed by the alternating addition of anionic and cationic polyelectrolytes to a wound or support. The term "polymer multilayer" also refers to the composition formed by sequential and repeated application of polymer(s) to a wound or to a solid support. In addition, the term "polymer layer" can refer to a single layer composed of polymer molecules, such as anionic or cationic polyelectrolyte molecules, existing either as one layer within multiple layers, or as a single layer of only one type of polyelectrolyte molecules on a wound or support. While the delivery of the polymers to the wound bed or support is sequential in preferred embodiments, the use of the term "polymer multilayer" is not limiting in terms of the resulting structure of the coating. It is well understood by those skilled in the art that inter-diffusion of polymers such as polyelectrolytes can take place leading to structures that may be well-mixed in terms of the distribution of anionic and cationic polyelectrolytes. It is also understood that the term polyelectrolyte includes polymer species as well as nanoparticulate species, and that it is not limiting in scope other than to indicate that the species possesses multiple charged or partially charged groups. It is also well understood by those skilled in the art that multilayer structures can be formed through a variety of interactions, including electrostatic interactions and others such as hydrogen bonding. Thus, the use of the term "polyelectrolyte" is not limiting in terms of the interactions leading to the formation of the wound bed constructs.

The term "subject" refers to any animal (e.g., a mammal), including, but not limited to, humans, non-human primates, rodents, dogs, cats, and the like, which is to be the recipient of a particular treatment. Typically, the terms "subject" and "patient" are used interchangeably herein.

The term "surfactant" refers to an amphiphilic material that modifies the surface and interface properties of liquids or solids. Surfactants can reduce the surface tension between two liquids. Detergents, wetting agents, emulsifying agents, dispersion agents, and foam inhibitors are all surfactants.

Figure 1:
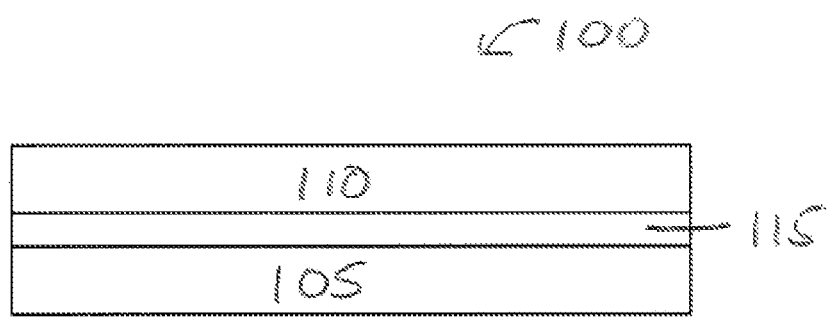
FIG. 1. Side view of a device of one embodiment of the invention.

The term "solvent" refers to a liquid that can dissolve a substance. The term "organic solvent" refers to a solvent derived from a petroleum-based product.

The term "polyelectrolyte" refers to a water-soluble macromolecular polymer substance containing many repeating ionic constituent units, including cations and anions.

The term "functionalized" refers to a modification of an existing molecular segment to generate or introduce a new reactive functional group (e.g., a maleimido or succinimidyl group) that is capable of undergoing reaction with another functional group (e.g., a sulfhydryl group) to form a covalent bond. For example, a component containing carboxylic acid (—COOH) groups can be functionalized by reaction with N-hydroxy-succinimide or N-hydroxysulfosuccinimide using known procedures, to form a new reactive functional group in the form of an activated carboxylate (which is a reactive electrophilic group), i.e., an N-hydroxysuccinimide ester or an N-hydroxysulfosuccinimide ester, respectively. In another example, carboxylic acid groups can be functionalized by reaction with an acyl halide, e.g., an acyl chloride, again using known procedures, to provide a new reactive functional group in the form of an anhydride.

As used herein, the term "aqueous solution" includes solutions, suspensions, dispersions, colloids, and the like containing water.

The term "specific protein binding" refers to an interaction between two or more proteins that have high affinity and specificity for each other. Proteins must bind to specific other proteins in vivo in order to function. The proteins are required to bind to only one or a few other proteins of the few thousand proteins typically present in vivo; these interactions are employed in vitro in the present invention to attach bioactive agents to the wound. In the context of the present invention, specific protein binding interactions include, but are not limited to, those between biotin and avidin, neutravidin, or streptavidin; glutathione-S-transferase and glutathione; and nickel-nitrilotriacetic acid and polyhistidine.

The term "device" refers to an object that contacts the body or bodily fluid of a subject for therapeutic or prophylactic purposes. Some devices may partially or indirectly contact the body or bodily fluid of a subject (e.g., catheter, dialysis tubing, diagnostic sensors, drug delivery devices), while other devices are completely imbedded in or encompassed by the body of a subject (e.g., stent, pacemaker, internally implanted defibrillator, angioplasty balloon, orthopedic device, spinal cage, implantable drug pump, artificial disc, ear disc).

The term "selective toxicity" refers to the property of differentially toxic effects on mammalian versus microbial cells. For example, a selectively toxic agent may effectively kill bacterial cells while permitting growth and viability of mammalian cells.

The term "toxic" refers to any detrimental or harmful effects on a subject, a cell, or a tissue as compared to the same cell or tissue prior to the administration of the toxicant.

As used herein, the terms "nanoparticle" and "nanoscale particles" are used interchangeably and refer to a nanoscale particle with a size that is measured in nanometers, for example, a nanoscopic particle that has at least one dimension of less than about 1000, 500, or 100 nm. Examples of nanoparticles include nanobeads, nanofibers, nanohorns, nano-onions, nanorods, and nanoropes.

As used herein, the term "microparticle" and "microscale particles" are used interchangeably and refers to a microscale particle with a size that is measured in micrometers, for example, a microscale particle that has at least one dimension of less than about 10 micrometers, 5 micrometers, or 2 micrometers.

The term "wound dressing" refers to materials placed proximal to a wound that have absorbent, adhesive, protective, osmoregulatory, pH-regulatory, or pressure-inducing properties. Wound dressings may be in direct or indirect contact with a wound. Wound dressings are not limited by size or shape. Indeed, many wound dressing materials may be cut or configured to conform to the dimensions of a wound. Examples of wound dressing materials include but are not limited to gauze, adhesive tape, bandages, and commercially available wound dressings including but not limited to adhesive bandages and pads from the Band-Aid® line of wound dressings, adhesive bandages and pads from the Nexcare® line of wound dressings, adhesive bandages and non-adhesive pads from the Kendall Curity Tefla® line of wound dressings, adhesive bandages and pads from the Tegaderm® line of wound dressings, adhesive bandages and pads from the Steri-Strip® line of wound dressings, the COMFEEL® line of wound dressings, adhesive bandages and pads, the Duoderm® line of wound dressings, adhesive bandages and pads, the TEGADERM™ line of wound dressings, adhesive bandages and pads, the OPSITE® line of wound dressings, adhesive bandages and pads, and biologic wound dressings. A "biologic wound dressing" is a type of wound dressing that comprises, e.g., is coated with or incorporates, cells and/or one or more biomolecules or fragments of biomolecules that can be placed in contact with the wound surface. The biomolecules may be provided in the form of an artificial tissue matrix. Examples of such biomolecules include, but are not limited, to collagen, hyaluronic acid, glycosaminoglycans, laminin, vitronectin, fibronectin, keratin, antimicrobial polypeptides and combinations thereof. Examples of suitable biologic wound dressings include, but are not limited to, BIOBRANE™, Integra™, Apligraf®, Dermagraft®, Oasis®, Transcyte®, Cryoskin® and Myskin®.

As used herein, the term "antimicrobial silver composition" refers to a composition that comprises silver as an active antimicrobial agent. Examples of "antimicrobial silver compositions" include, but are not limited to silver nanoparticles, elemental silver, zero valent silver, multivalent silver ions carried by zirconium phosphate (ZP—Ag) (See, e.g., Wound Repair and Regeneration, 16: 800-804), and silver containing compounds such as silver sulfadiazine and related compounds. The term "releasable antimicrobial silver composition" refers to a antimicrobial silver composition that can be released from a material, for example, a polymeric multilayer solid support, so that antimicrobial activity can be observed. The release of the antimicrobial silver composition can be defined as an amount of the composition released from a defined area or volume of the material.

DETAILED DESCRIPTION OF THE INVENTION

The present invention provides devices for application to wounds comprising multiple adjacent polymer layers containing antimicrobial and analgesic agents. The devices provided find use in application to a wound, a biologic tissue, a cornea, a lens, a bone, a tendon, a surgical mesh, a wound dressing, a biomedical device, a device used for healthcare, or other surface.

Figure 2:
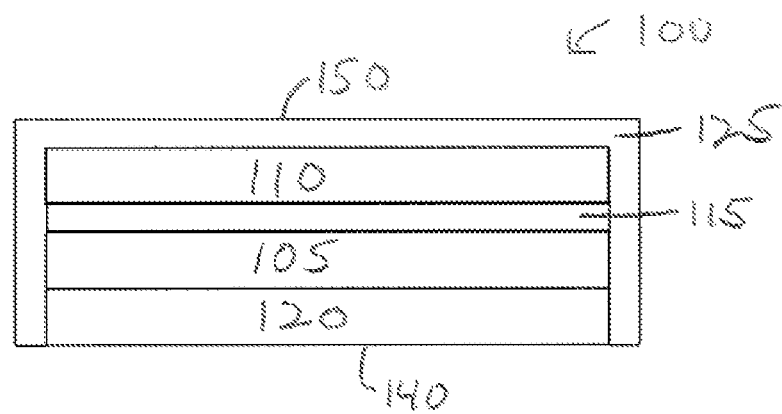
FIG. 2. Side view of a device of another embodiment of the invention.
Figure 3:
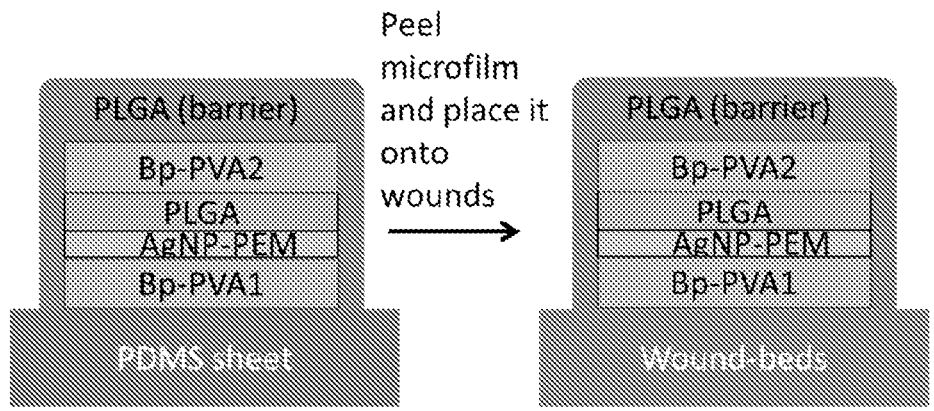
FIG. 3. Schematic illustration of one embodiment of the delivery platform comprised of a microfilm construct containing Bp (within each of the two PVA films within the platform) and AgNP (within a nanofilm) that can be placed over a wound surface. The top layer of PLGA is used to direct the fluxes of Bp and Ag ions release from their host layers toward wound surface (and hence prevent the loss of agents in the overlying wound fluid). The middle PLGA layer is designed to control diffusion of Bp from the top PVA film, hence providing a sustained release of Bp toward wound sites following the burst release of Bp from the bottom most PVA.
Figure 4:
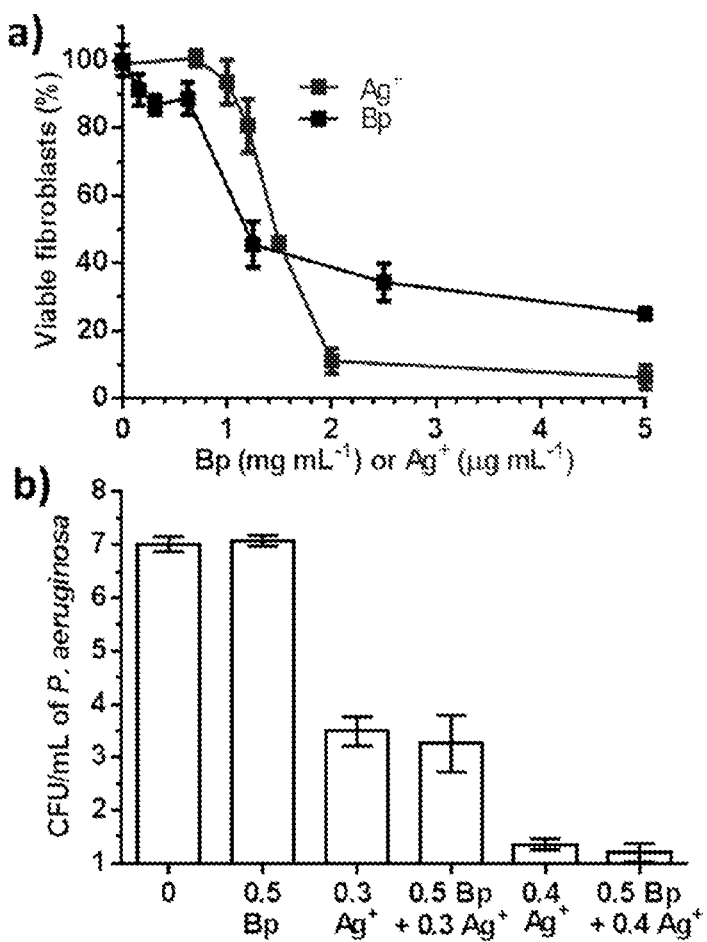
Figure 5:
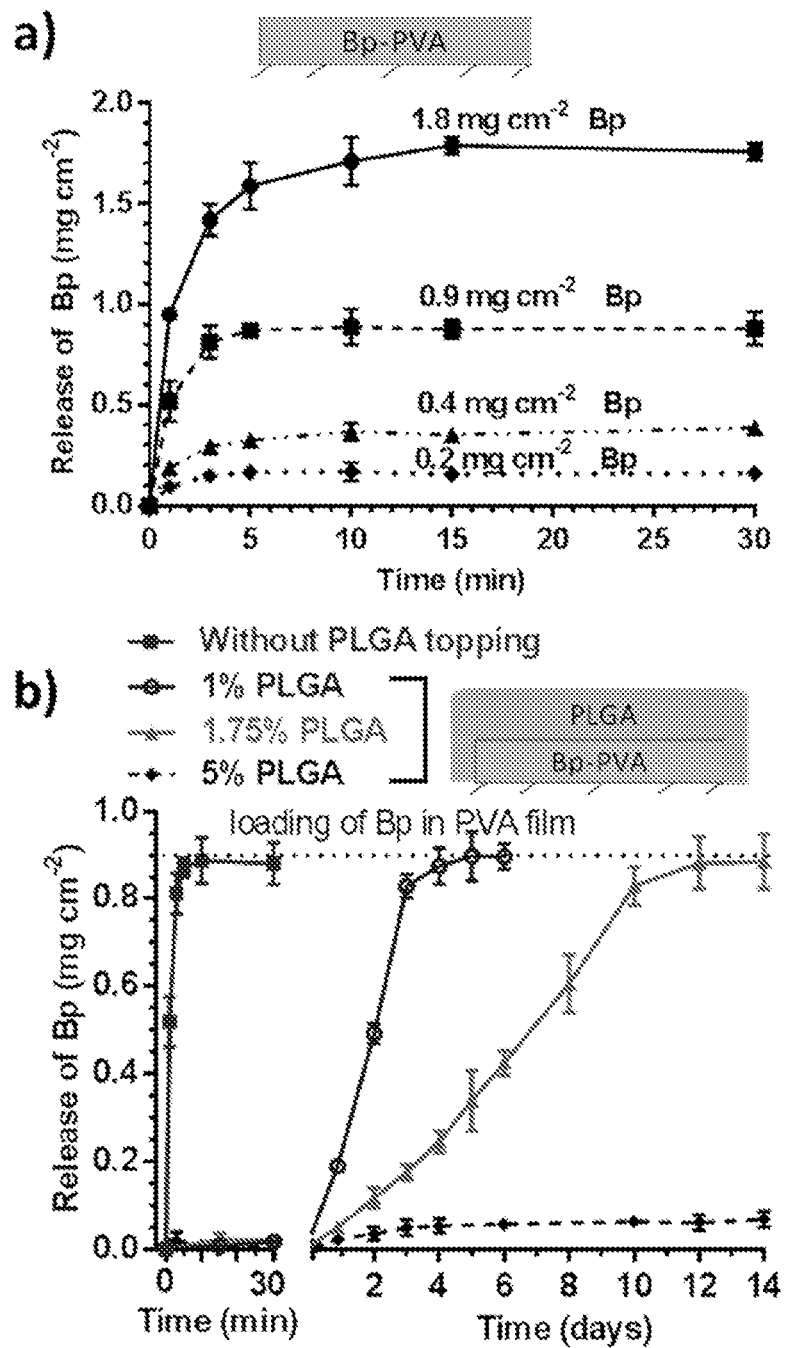

Referring to FIGS. 1 and 2, in some embodiments, a device of the present invention 100 comprises a first polymer layer 105 comprising a first bioactive agent. In preferred embodiments, the first bioactive agent is an antimicrobial agent. The first polymer layer 105 may be alternatively referred to the antimicrobial polymer layer of antimicrobial polymer multilayer. In some preferred embodiments, the first polymer layer 105 is a nanoscale polymer multilayer. In some embodiments, the nanoscale polymer multilayer is from about 1 nm to 10000 nm thick, from about 1 nm to 5000 nm thick, from about 1 nm to 500 nm thick, from about 1 nm to 100 nm thick, from about 1 nm to about 25 nm thick, from about 1 nm to about 10 nm thick, or less than about 500 nm, 100 nm, 25 nm or 10 nm thick. It is contemplated that the nanoscale dimension of the matrices (i.e., the nanoscale thickness) allows for the loading of a lower total amount of an antimicrobial agent while still allowing delivery of an effective amount (i.e., an amount of antimicrobial agent that prevents or inhibits infection as compared to controls) of the active agent as compared to matrix structures with greater thickness. It is contemplated that the lower total loading levels result in reduced toxicity in the wound environment, especially when antimicrobial compounds are incorporated into the polymer multilayer. Suitable polymers for the nanoscale polymer multilayers and antimicrobial agents are described in detail below.

In some embodiments, the device 100 further comprises a second polymer layer 110 comprising a second bioactive agent. In some preferred embodiments, the second bioactive agent is an analgesic agent. The second polymer layer 110 may be alternatively referred to as the first analgesic polymer layer. In some preferred embodiments, the second polymer layer 110 is a microscale polymer layer. In some embodiments, the second microscale polymer layer 110 is from about 1 µm to 500 µm thick, from about 1 µm to 100 nm thick, from about 10 µm to 100 µm thick, from about 10 µm to 80 µm thick, or from about 30 µm to about 60 µm thick. In some preferred embodiments, the second polymer layer 110 is formed from a different polymer than the first polymer layer. In some particularly preferred embodiments, the second polymer layer 110 is formed from a water soluble polymer. Suitable polymers for use in the second polymer layer 110 and analgesic agents are described in detail below.

In some preferred embodiments, the first and second polymer layers 105 and 110 are adjacent to one another. In other preferred embodiments, the first and second polymer layers 105 and 110 are separated by a third polymer layer 115. The third polymer layer 115 may alternatively be referred to as the inner barrier polymer layer. In some preferred embodiments, the third polymer layer 115 is a microscale polymer layer. In some embodiments, the third microscale polymer layer 115 is from about 1 µm to 500 µm thick, from about 1 µm to 100 nm thick, from about 10 µm to 100 µm thick, from about 10 µm to 80 µm thick, or from about 20 µm to about 40 µm thick. In some preferred embodiments, the third polymer layer 115 is formed from a different polymer than the first and second polymer layers 105 and 110. In some particularly preferred embodiments, the third polymer layer 115 is formed from a water soluble polymer that is different from the polymer utilized in the second layer 110. In some preferred embodiments, the third polymer layer 115 does not comprise a bioactive agent (e.g., an antimicrobial or analgesic agent). Suitable polymers for use in the third polymer layer 115 are described in detail below.

The devices of the present invention are not limited to any particular arrangement of the polymer layers, number of polymer layers, or first and second bioactive agents. For example, referring to FIG. 2, in still further preferred embodiments, the device 100 may further comprise a fourth polymer layer 120 adjacent to the first polymer layer. The fourth polymer layer 120 may preferably comprise an analgesic agent and is preferably formed from the same polymer as the second polymer layer, but may be formed from a different polymer. The fourth polymer layer 120 may alternatively be referred to as the second analgesic polymer layer. Like the second polymer layer 110, the fourth polymer layer 120 is preferably a microscale polymer layer. In some embodiments, the fourth microscale polymer layer 120 is from about 1 µm to 500 µm thick, from about 1 µm to 100 nm thick, from about 10 µm to 100 µm thick, from about 10 µm to 80 µm thick, or from about 30 µm to about 60 µm thick. In some particularly preferred embodiments, the fourth polymer layer 120 is formed from a water soluble polymer. In some preferred embodiments, the forth polymer layer 120 is on the wound surface side 140 of the device and contacts the wound surface when the device is applied a wound. Suitable polymers for use in the fourth polymer layer 120 and analgesic agents are described in detail below.

In still other preferred embodiments, the device 100 of the present invention may further comprise a fifth polymer layer 125 (also referred to as the outer barrier polymer layer). The fifth polymer layer 125 is preferably adjacent to the second polymer layer 110 on the exposed side 150 of the device. In embodiments where included, the fifth polymer layer 125 provides an outer barrier that is oriented away from the surface of the wound and exposed to the environment. The fifth polymer layer 125 is preferably a microscale polymer layer formed from a water soluble polymer. In some preferred embodiments, the polymer used to form the fifth polymer layer 125 is the same polymer as used to form the third polymer layer 115, however, a different polymer may also be used. In some preferred embodiments, the fifth polymer layer is from about 50 µm to 1000 µm thick, from about 50 µm to 500 nm thick, from about 50 µm to 250 µm thick, from about 50 µm to 200 µm thick, or from about 80 µm to about 150 µm thick. Suitable polymers for use in the fifth polymer layer 125 are described in detail below.

As described above, in some embodiments, the devices of the present invention include a nanoscale polymer layer, preferably a nanoscale polymer multilayer. In some embodiments, the multilayer structures comprise layers of polyelectrolytes (i.e., forming a polyelectrolyte multilayer), while in other embodiments, the multilayers comprise polymers that do not have a charge (i.e., non-ionic polymers) or a combination of charged and uncharged polymer layers. In some embodiments, it is contemplated that polyelectrolyte films built-up by the alternated adsorption of cationic and anionic polyelectrolyte layers constitute a novel and promising technique to modify wound surfaces in a controlled way (Decher et al., 1992, Thin Solid Films 210/211:831; Decher, 1997, Science 277:1232). One of the most important properties of such multilayers is that they exhibit an excess of alternatively positive and negative charges (Caruso et al., 1999, J Am Chem Soc 121:6039; Ladam et al., 2000, Langmuir 16:1249). Not only can this constitute the motor of their buildup (Joanny, 1999, Eur. Phys. J. Biol. 9:117), but it allows, by simple contact, to adsorb a great variety of compounds such as dyes, particles (Cassagneau et al., 1998, J. Am. Chem. Soc. 120:7848; Caruso et al., 1999, Langmuir 15:8276; Lvov et al., 1997, Langmuir 13:6195), clay microplates (Ariga et al., 1999, Appl. Clay Sci. 15:137) and proteins (Keller et al., 1994, J. Am. Chem. Soc. 116:8817; Lvov et al., 1995, J. Am. Chem. Soc. 117:6117; Caruso et al., 1997, Langmuir 13:3427).

Polyelectrolyte layers are formed by alternating applications of anionic polyelectrolytes and cationic polyelectrolytes to surfaces to form a polyelectrolyte multilayer. In some embodiments, one or more bioactive agents, such as those described above, are incorporated into the multilayer. Preferably, at least four layers, and, more preferably, at least six layers are used to form the polyelectrolyte multilayer.

Cationic polyelectrolytes useful in the present invention can be any biocompatible water-soluble polycationic polymer, for example, any polymer having protonated heterocycles attached as pendant groups. As used herein, "water soluble" means that the entire polymer must be soluble in aqueous solutions, such as buffered saline or buffered saline with small amounts of added organic solvents as co-solvents, at a temperature between 20 and 37° Centigrade. In some embodiments, the material will not be sufficiently soluble (defined herein as soluble to the extent of at least one gram per liter) in aqueous solutions per se but can be brought into solution by grafting the polycationic polymer with water-soluble polynonionic materials such as polyethylene glycol.

Representative cationic polyelectrolytes include natural and unnatural polyamino acids having net positive charge at neutral pH, positively charged polysaccharides, and positively charged synthetic polymers. Examples of suitable polycationic materials include polyamines having amine groups on either the polymer backbone or the polymer side chains, such as poly-L-lysine (PLL) and other positively charged polyamino acids of natural or synthetic amino acids or mixtures of amino acids, including, but not limited to, poly(D-lysine), poly(ornithine), poly(arginine), and poly(histidine), and nonpeptide polyamines such as poly(aminostyrene), poly(aminoacrylate), poly (N-methyl aminoacrylate), poly (N-ethylaminoacrylate), poly(N,N-dimethyl aminoacrylate), poly(N,N-diethylaminoacrylate), poly(aminomethacrylate), poly(N-methyl amino-methacrylate), poly (N-ethyl aminomethacrylate), poly(N,N-dimethyl aminomethacrylate), poly(N,N-diethyl aminomethacrylate), poly(ethyleneimine), polymers of quaternary amines, such as poly(N,N,N-trimethylaminoacrylate chloride), poly(m-ethyacrylamidopropyltrimethyl ammonium chloride), and natural or synthetic polysaccharides such as chitosan.

Polyanionic materials useful in the present invention can be any biocompatible water-soluble polyanionic polymer, for example, any polymer having carboxylic acid groups attached as pendant groups. Suitable materials include alginate, carrageenan, furcellaran, pectin, xanthan, hyaluronic acid, heparin, heparan sulfate, chondroitin sulfate, polyacrylic acid (PAA), dermatan sulfate, dextran sulfate, poly(meth)acrylic acid, oxidized cellulose, carboxymethyl cellulose and crosmarmelose, synthetic polymers and copolymers containing pendant carboxyl groups, such as those containing maleic acid or fumaric acid in the backbone. Polyaminoacids of predominantly negative charge are also suitable. Examples of these materials include polyaspartic acid, polyglutamic acid, and copolymers thereof with other natural and unnatural amino acids. Polyphenolic materials such as tannins and lignins can be used if they are sufficiently biocompatible. Preferred materials include alginate, pectin, carboxymethyl cellulose, heparin and hyaluronic acid.

In some embodiments, the cationic polyelectrolyte used is PLL and the anionic polyelectrolyte used is poly(L-glutamic acid) (PGA). In some further preferred embodiments, the cationic polyelectrolyte used is polyallylamine hydrochloride (PAH) and the anionic polyelectrolyte used is polyacrylic acid (PAA). Indeed, the use of a variety of polyelectrolytes is contemplated, including, but not limited to, poly(ethylene imine) (PEI), poly(sodium 4-styrenesulfonate) (PSS), poly(acrylic acid) (PAC), poly(maleic acid-co-propylene) (PMA-P), and poly(vinyl sulfate) (PVS). It is also possible to use naturally occurring polyelectrolytes, including hyaluronic acid and chondroitin sulfate. In still further embodiments, the polymer is a dendrimer, grafted polymer, or star architecture polymer.

In some embodiments, the multilayer structures are formed from uncharged polymers or from a combination of charged and uncharged polymers. Examples of uncharged polymers include, but are not limited to, dextran, dextran sulfate, diethylaminoethyl (DEAE)-dextran, hydroxyethyl cellulose, ethyl(hydroxyethyl) cellulose, acrylamide, polyethylene oxide, polypropylene oxide, polyethylene oxide-polypropylene oxide copolymers, $PAAN_a$, Ficoll, polyvinylpyrolidine, and polyacrylic acid.

In some embodiments, the multilayer structures are formed from one or more amphoteric polymers, alone in combination with the other polymers described herein. In some embodiments, the amphoteric polymers comprise one or more of acrylic acid (AA), DMAEMA (dimethylaminoethyl methacrylate), APA (2-aminopropyl acrylate), MorphEMA (morpholinoethyl methacrylate), DEAEMA (diethylaminoethyl methacrylate), t-ButylAEMA (t-butylaminoethyl methacrylate), PipEMA (piperidinoethyl methacrylate), AEMA (aminoethyl methacrylate), HEMA (2-hydroxyethyl methacrylate), MA (methyl acrylate), MAA (methacrylic acid) APMA (2-aminopropyl methacrylate), AEA (aminoethyl acrylate). In some embodiments, the amphoteric polymer comprises (a) carboxylic acid, (b) primary amine, and (c) secondary and/or tertiary amine. The amphoteric polymers have an isoelectric point of 4 to 8, preferably 5 to 7 and have a number average molecular weight in the range of 10,000 to 150,000.

As described above, in some embodiments, the devices of the present invention include one or more microscale polymer layers that can include or not include a second bioactive agent. As described above, in some embodiments, the microscale polymer layer or layers that include the second bioactive agent are formed from a different polymer than the microscale polymer layers or layers that do not include a bioactive agent. In some preferred embodiments, the microscale polymer layers are formed from biocompatible polymers. In some preferred embodiments, the biocompatible polymers are dissolvable and most preferably water soluble. Suitable polymers for use in the microscale polymer layers include, but are not limited to, polyvinyl alcohol (PVA), polyacrylic acid (PAA), polyvinylpyrrolidone (PVP), carboxymethyl cellulose (CMC), sodium carboxymethyl cellulose, methylcellulose, ethylcellulose, ethylmethyl cellulose, hydroxyethyl cellulose (HEC), hydroxylpropyl cellulose (HPC), hydroxypropyl methylcellulose (HPMC), alginates, polyvinylacetate (PVAc), polylactic acid (PLA), polylactic-co-glycolic acid (PLGA), polyglycolic acid, and polyanhydrides. In some particularly preferred embodiments, microscale polymer layers that include the second bioactive agent are formed from PVA, while the microscale polymer layers that do not include a bioactive agent are formed from PLGA.

It is contemplated that the devices of the present invention may incorporate a wide variety of first and second bioactive agents. Bioactive agents that may be desirable to deliver via the devices of the present invention include, but are not limited to, anti-infective agents (including antimicrobials, antivirals and antifungals), analgesics including local anesthetics, trophic factors, enzymes, enzyme inhibitors, defensins, polypeptides, anticoagulants, coagulation factors, anti-inflammatory agents, vasoconstrictors, vasodilators, diuretics, and anti-cancer agents.

In some embodiments, the first or second bioactive agent is an analgesic agent, including, but not limited to, acetaminophen, anileridine, acetylsalicylic acid, buprenorphine, butorphanol, fentanyl, fentanyl citrate, codeine, rofecoxib, hydrocodone, hydromorphone, hydromorphone hydrochloride, levorphanol, alfentanil hydrochloride, meperidine, meperidine hydrochloride, methadone, morphine, nalbuphine, opium, levomethadyl, hyaluronate sodium, sufentanil citrate, capsaicin, tramadol, leflunomide, oxycodone, oxymorphone, celecoxib, pentazocine, propoxyphene, benzocaine, lidocaine, dezocine, clonidine, butalbital, phenobarbital, tetracaine, phenazopyridine, sulfamethoxazole/phenazopyridine, and sulfisoxazole/phenazopyridine.

In some embodiments, the analgesic agent is a local anesthetic, including, but not limited to, amylocaine, ambucaine, articaine, benzocaine, benzonatate, bupivacaine, butacaine, butanilicaine, chloroprocaine, cinchocaine, cyclomehtycaine, dibucaine, diperodon, dimethisoquin, dimethocaine, eucaine, etidocaine, hexylcaine, fomocaine, fotocaine, hydroxyprocaine, isobucaine, levobupivicaine, iodocaine, mepivacaine, meprylcaine, metabutoxycaine, nitracaine, orthocaine, oxetacaine, oxybuprocaine, paraethocycaine, phenacaine, piperocaine, piridocaine, pramocaine, prilocaine, primacaine, procaine, procainamide, proparacaine, propoxycaine, pyrrocaine, quinisocaine, ropivacaine, trimecaine, tetracaine, tolycaine, and tropacocaine.

In some embodiments, the first or second bioactive agent is an opioid antagonist and/or mixed opioid agonist/antagonist (which may also be opioid analgesic as is known in the art), including, but not limited to, naloxone, diprenorphine, naltrexone, buprenorphine, bupremorphine/naloxone, nalodeine, nalorphine, levallorphan, nalmefene, naloxol, alvimopan, naldemedine, eluxadoline, asimadoline, naloxegol, methylnaltrexone, dezocine, naloxegol, eptazocine, butorphanol, levorphanol, nalbuphine, pentazocine, phenazocine, cyprodime, naltrindole, norbinaltorphimine, and J113,393.

In some embodiments, the first or second bioactive agent is an antimicrobial agent, including, but not limited to, loracarbef, cephalexin, cefadroxil, cefixime, ceftibuten, cefprozil, cefpodoxime, cephradine, cefuroxime, cefaclor, neomycin/polymyxin/bacitracin, dicloxacillin, nitrofurantoin, nitrofurantoin macrocrystal, nitrofurantoin/nitrofuran mac, dirithromycin, gemifloxacin, ampicillin, gatifloxacin, penicillin V potassium, ciprofloxacin, enoxacin, amoxicillin, amoxicillin/clavulanate potassium, clarithromycin, levofloxacin, moxifloxacin, azithromycin, sparfloxacin, cefdinir, ofloxacin, trovafloxacin, lomefloxacin, methenamine, erythromycin, norfloxacin, clindamycin/benzoyl peroxide, quinupristin/dalfopristin, doxycycline, amikacin sulfate, vancomycin, kanamycin, netilmicin, streptomycin, tobramycin sulfate, gentamicin sulfate, tetracyclines, framycetin, minocycline, nalidixic acid, demeclocycline, trimethoprim, miconazole, colistimethate, piperacillin sodium/tazobactam sodium, paromomycin, colistin/neomycin/hydrocortisone, amebicides, sulfisoxazole, pentamidine, sulfadiazine, clindamycin phosphate, metronidazole, oxacillin sodium, nafcillin sodium, vancomycin hydrochloride, clindamycin, cefotaxime sodium, co-trimoxazole, ticarcillin disodium, piperacillin sodium, ticarcillin disodium/clavulanate potassium, neomycin, daptomycin, cefazolin sodium, cefoxitin sodium, ceftizoxime sodium, penicillin G potassium and sodium, ceftriaxone sodium, ceftazidime, imipenem/cilastatin sodium, aztreonam, cinoxacin, erythromycin/sulfisoxazole, cefotetan disodium, ampicillin sodium/sulbactam sodium, cefoperazone sodium, cefamandole nafate, gentamicin, sulfisoxazole/phenazopyridine, tobramycin, lincomycin, neomycin/polymyxin B/gramicidin, clindamycin hydrochloride, lansoprazole/clarithromycin/amoxicillin, alatrofloxacin, linezolid, bismuth subsalicylate/metronidazole/tetracycline, erythromycin/benzoyl peroxide, mupirocin, fosfomycin, pentamidine isethionate, imipenem/cilastatin, troleandomycin, gatifloxacin, chloramphenicol, cycloserine, neomycin/polymyxin B/hydrocortisone, ertapenem, meropenem, cephalosporins, fluconazole, cefepime, sulfamethoxazole, sulfamethoxazole/trimethoprim, neomycin/polymyxin B, penicillins, rifampin/isoniazid, erythromycin estolate, erythromycin ethylsuccinate, erythromycin stearate, ampicillin trihydrate, ampicillin/probenecid, sulfasalazine, sulfanilamide, sodium sulfacetamide, dapsone, doxycycline hyclate, trimenthoprim/sulfa, methenamine mandelate, plasmodicides, pyrimethamine, hydroxychloroquine, chloroquine phosphate, trichomonocides, anthelmintics, atovaquone, bacitracin, bacitracin/polymyxin b, gentamycin, neomycin/polymyxin/dexameth, neomycin sulf/dexameth, sulfacetamide/prednisolone, sulfacetamide/phenylephrine, tobramycin sulfate/dexameth, bismuth tribromophenate, silver ion compounds, silver nanoparticles, zerovalent silver, multivalent silver, elemental silver, and silver containing compounds such as silver sulfadiazine and related compounds, gallium ion compounds, gallium ion salts, a gallium ion nanoparticles, alloys of gallium, and alloys of gallium and silver.

Some particularly preferred antimicrobial agents include chlorhexidine, iodine based antimicrobials such as PVP-iodine; selenium based antimicrobials such as 7-azabenzisoselenazol-3(2H)-ones, selenium disulfide, and selenides; silver based antimicrobials (e.g., silver sulfadiazine, ionic silver, elemental silver, silver nanoparticles)) and gallium based antimicrobials.

In some embodiments, the first or second bioactive agent is an antiviral agent, including, but not limited to, amantadine, acyclovir, foscarnet, indinavir, ribavirin, enfuvirtide, emtricitabine, lamivudine, abacavir sulfate, fomivirsen, valacyclovir, tenofovir, cidofovir, atazanavir, amprenavir, delavirdine mesylate, famciclovir, adefovir, didanosine, efavirenz, trifluridine, inidinavir, lamivudine, vidarabine, lopinavir/ritonavir, ganciclovir, zanamivir, abacavir/lamivudine/zidovudine, lamivudine/zidovudine, nelfinavir, nelfinavir mesylate, nevirapine, ritonavir, saquinavir, saquinavir mesylate, rimantadine, stavudine, docosanol, zalcitabine, idoxuridine, zidovudine, zidovudine/didanosine, valganciclovir, penciclovir, lamivudine, and oseltamivir.

In some embodiments, the first or second bioactive agent is an antifungal agent, including, but not limited to, amphotericin B, nystatin, nystatin/triamcinolone, itraconazole, ketoconazole, miconazole, sulconazole, clotrimazole, clotrimazole/betamethasone, enilconazole, econazole, oxiconazole, tioconazole, terconazole, butoconazole, thiabendazole, flucytosine, butenafine, ciclopirox, haloprogin, naftifine, tolnaftate, natamycin, undecylenic acid, mafenide, dapsone, clioquinol, clioquinol/hydrocortisone, potassium iodide, silver sulfadiazine, gentian violet, carbol-fuchsin, cilofungin, sertaconazole, voriconazole, fluconazole, terbinafine, caspofungin, other topical azole drugs, and griseofulvin.

In some embodiments, the first or second bioactive agent is a trophic factor, including, but not limited to, agrin, amphiregulin, artemin, cardiotrophin-1, epidermal growth factors including EGF; fibroblast growth factors (e.g., FGF-1, FGF-2, FGF-3, FGF-4, FGF-5, FGF-6, and FGF-7); LIF, CSF-1, CSF-2, CSF-3, erythropoietin, endothelial cell growth factors including ECGF; FGF-related and ECGF-related growth factors (e.g., endothelial cell stimulating angiogenesis factor, tumor angiogenesis factor, retina-derived growth factor (RDGF), vascular endothelium growth factor (VEGF), brain-derived growth factors (BDGF-A and B), astroglial growth factors (AGF 1 and 2), omentum-derived growth factor, fibroblast-stimulating factor (FSF), and embryonal carcinoma-derived growth factor (ECDGF)); neurotrophic growth factors (e.g, nerve growth factors (NGFs), neurturin, brain-derived neurotrophic factor (BDNF), neurotrophin-3, neurotrophin-4, and ciliary neurotrophic factor (CNTF)); glial growth factors (e.g., GGF-I, GGF-II, GGF-III, glia maturation factor (GMF), and glial-derived neurotrophic factor (GDNF)); liver growth factors (e.g., hepatopoietin A, hepatopoietin B, and hepatocyte growth factors including HGF); prostate growth factors including prostate-derived growth factors (PGFs); mammary growth factors including mammary-derived growth factor 1 (MDGF-1) and mammary tumor-derived factor (MTGF); heart growth factors including nonmyocyte-derived growth factor (NMDGF); melanocyte growth factors including melanocyte-stimulating hormone (MSH) and melanoma growth-stimulating activity (MGSA); angiogenic factors (e.g., angiogenin, angiotropin, platelet-derived ECGF, VEGF, and pleiotrophin); transforming growth factors including TGF-α and TGF-β; TGF-like growth factors (e.g., TGF-beta$_1$, TGF-beta$_2$, TGF-beta$_3$, GDF-1, CDGF, tumor-derived TGF-like factors, ND-TGF, and human epithelial transforming factor); regulatory peptides with growth factor-like properties (e.g., bombesin and bombesin-like peptides ranatensin and litorin, angiotensin, endothelin, atrial natriuretic factor, vasoactive intestinal peptide, and bradykinin); platelet-derived growth factors including PDGF-A, PDGF-B, and PDGF-AB; neuropeptides (e.g., substance P, calcitonin gene-regulated peptide (CGRP), and neuropeptide Y); neurotransmitters and their analogs including norepinephrine, acetylcholine and carbachol; hedgehog, heregulin/neuregulin, IL-1, osteoclast-activating factor (OAF), lymphocyte-activating factor (LAF), hepatocyte-stimulating factor (HSF), B-cell-activating factor (BAF), tumor inhibitory factor 2 (TIF-2), keratinocyte-derived T-cell growth factor (KD-TCGF), IL-2, IL-3, IL-4, IL-5, IL-6, IL-7, IL-8, IL-9, IL-10, IL-11, stromal cell-derived cytokine (SCDC), IL-12, IL-13, IL-14, IL-15, insulin, insulin-like growth factors including IGF-1, IGF-2, and IGF-BP; interferons including INF-alpha, INF-beta, and INF-gamma; leptin, midkine, tumor necrosis factors (TNF-alpha and beta), netrins, saposins, semaphorins, somatrem, somatropin, stem cell factor, VVGF, bone morphogenetic proteins (BMPs), adhesion molecules, other cytokines, heparin-binding growth factors, and tyrosine kinase receptor ligands. In some embodiments, the bioactive agent is a peptide such as AcEEED, which is the N terminal peptide for alpha smooth muscle actin and has been shown to inhibit contractile properties of myofibroblasts.

In some embodiments, the first or second bioactive agent is an ECM (extra cellular matrix component, including, but not limited to native constructs, fragments of native constructs and synthetic analogs of: extracellular matrix proteins, reconstituted basement membrane-like complexes derived from eukaryotic cell lines, collagens, fibronectin, laminin, VCAM-1, vitronectin and gelatin, a bacterial extracellular matrix, a gel matrix, and polymeric matrices. In some embodiments, the bioactive agents are integrin binding sequences exemplified by, but not limited to RGD, EILDV, VCAM-1 and their recombined or synthetic analogs, enzymes, enzyme inhibitors, and polypeptides.

In some embodiments, the first or second bioactive agent is an enzyme, including, but not limited to, exopeptidases and endopeptidases (also known as proteases and proteinases), including but not limited to the serine proteinases chymotrypsin, trypsin, elastase, and kallikrein, bacterial enzymes, the cysteine proteases papain, actinin, bromelain, cathepsins, cytosolic calpains, parasitic proteases, aspartic proteinases, the pepsin family of proteases pepsin and chymosin, lysosomal cathepsins D, renin, fungal proteases, the viral proteases, AIDS virus retropepsin, and the metalloproteinases (MMPs), collagenases, Maggott enzyme, MMP1, MMP2, MMP8, MMP13, gelatinases, MMP2, MMP9, MMP3, MMP7, MMP10, MMP11, and MMP12.

In some embodiments, the first or second bioactive agent is an enzyme inhibitor, including, but not limited to captopril, thiorphan, phosphoramidon, teprotide, protease and proteinase inhibitors, metalloproteinase inhibitors and exopeptidase inhibitors.

In some embodiments, the first or second bioactive agent is a polypeptide, including, but not limited to, fibronectin, serotonin, PAF, PDEGF, TNFa, IL1 IL6, IGF, IGF-1, IGF-2, IL-1, PDGF, FGF, KGF, VEGF, bradykinin, prothymosin-alpha, and thymosin-alpha1.

In some embodiments, the first or second bioactive agent is an antimicrobial polypeptide, including, but not limited to, alpha-defensins HNP 1, 2, 3 and 4, and beta-defensins HBD-1 and HBD-2, cathelicidins, magainin (e.g., magainin I, magainin II, xenopsin, xenopsin precursor fragment, caerulein precursor fragment), magainin I and II analogs (e.g., PGLa, magainin A, magainin G, pexiganin, Z-12, pexigainin acetate, D35, MSI-78A, MG0 (K10E, K11E, F12W-magainin 2), MG2+ (K10E, F12W-magainin-2), MG4+ (F12W-magainin 2), MG6+ (f12W, E19Q-magainin 2 amide), MSI-238, reversed magainin II analogs (e.g., 53D, 87-ISM, and A87-ISM), Ala-magainin II amide, magainin II amide), cecropin P1, cecropin A, cecropin B, indolicidin, nisin, ranalexin, lactoferricin B, poly-L-lysine, cecropin A (1-8)-magainin II (1-12), cecropin A (1-8)-melittin (1-12), CA(1-13)-MA(1-13), CA(1-13)-ME(1-13), gramicidin, gramicidin A, gramicidin D, gramicidin S, alamethicin, protegrin, histatin, dermaseptin, lentivirus amphipathic peptide or analog, parasin I, lycotoxin I or II, globomycin, gramicidin S, surfactin, ralinomycin, valinomycin, polymyxin B, PM2 ((+/−) 1-(4-aminobutyl)-6-benzylindane), PM2c ((+/−) -6-benzyl-1-(3-carboxypropyl)indane), PM3 ((+/−)1-benzyl-6-(4-aminobutyl)indane), tachyplesin, buforin I or II, misgurin, melittin, PR-39, PR-26, 9-phenylnonylamine, (KLAKKLA)n, (KLAKLAK)n, where n=1, 2, or 3, (KALKALK)3, KLGKKLG)n, and KAAKKAA)n, wherein N=1, 2, or 3, paradaxin, Bac 5, Bac 7, ceratoxin, mdelin 1 and 5, bombin-like peptides, PGQ, cathelicidin, HD-5, Oabac5alpha, ChBac5, SMAP-29, Bac7.5, lactoferrin, granulysin, thionin, hevein and knottin-like peptides, MPG1, lbAMP, snakin, lipid transfer proteins, and plant defensins. In some embodiments, the antimicrobial peptides are synthesized from L-amino acids, while in other embodiments, the peptides are synthesized from, or comprise, D-amino acids.

In some embodiments, the first or second bioactive agent is a buffering agent, including, but not limited to, Maleic acid, Phosphoric acid, Glycine, Chloroacetic acid, Formic acid, Benzoic acid, Acetic acid, Pyridine, Piperazine, MES, Bis-tris, Carbonate, ACES, ADA MOPSO, PIPES, Phosphoric acid, BES, MOPS, TES, HEPES, DIPSO, TAPSO, Triethanolamine, HEPSO, Tris, Tricine, Bicine, TAPS, Borate, Ammonia, CHES, Ethanolamine, CAPSO, Glycine, Carbonate, CAPS, Methylamine, Piperidine, and Phosphoric acid.

In some embodiments, the first or second bioactive agent is a vitamin or mineral, including, but not limited to, Vitamin A, Carotenoids, Vitamin D, Vitamin E, Vitamin K, Vitamin C/ascorbic acid, B1/thiamin, B2/riboflavin, B3/niacin, B5/pantothenic acid, B6/pyridoxine, B12/cobalamin, Biotin, Calcium, Magnesium, Phosphorus, Sodium, Chloride, Potassium, Boron, Chromium, Copper, Iodine, Iron, Manganese, Selenium, and Zinc.

In some embodiments, the first or second bioactive agent is an anticoagulant, including, but not limited to, coumarins, 1,3-indandione, anisindione, fondaparinux, heparin, lepirudin, antithrombin, warfarin, enoxaparin, dipyridamole, dalteparin, ardeparin, nadroparin, and tinzaparin.

In some embodiments, the first or second bioactive agent is a coagulation factor, including, but not limited to, Factor I (fibrinogen), Factor II (prothrombin), Factor III (thromboplastin, tissue factor), Factor IV (calcium), Factor V (labile factor), Factor VII (stable factor), Factor VIII (antihemophilic globulin, antihemophilic globulin, antihemophilic factor A), Factor IX (plasma thromboplastin component, Christmas factor, antihemophilic factor B), Factor X (Stuart factor, Prower factor, Stuart-Prower factor), Factor XI (plasma thromboplastin antecedent, antihemophilic factor C), Factor XII (Hageman factor, surface factor, contact factor), and Factor XIII (fibrin stabilizing factor, fibrin stabilizing enzyme, fibri-nase).

In some embodiments, the first or second bioactive agent is an anti-inflammatory agent, including, but not limited to, non steroidal anti-inflammatory drugs (NSAIDs) including diclofenac (also known as Voltaren, Abitren, Allvoran, Almiral, Alonpin, Anfenax, Artrites, Betaren, Blesin, Bolabomin, Cataflam, Clofec, Clofen, Cordralan, Curinflam, Diclomax, Diclosian, Dicsnal, Difenac, Ecofenac, Hizemin, Inflamac, Inflanac, Klotaren, Lidonin, Monoflam, Naboal, Oritaren, Remethan, Savismin, Silino, Staren, Tsudohmin, Voltarol, Voren, Voveran, and Vurdon), diflunisal (also known as Dolobid, Adomal, Diflonid, Diflunil, Dolisal, Dolobis, Dolocid, Donobid, Dopanone, Dorbid, Dugodol, Flovacil, Fluniget, Fluodonil, Flustar, Ilacen, Noaldol, Reuflos, and Unisal), etodolac (also known as Lodine), fenoprofen (also known as Nalfon, Fenoprex, Fenopron, Fepron, Nalgesic, and Progesic), flurbiprofen (also known as Ansaid and Ocuflur), ibuprofen (also known as Rufen, Motrin, Aches-N-Pain, Advil, Nuprin, Dolgesic, Genpril, Haltran, Ibifon, Ibren, Ibumed, Ibuprin, Ibupro-600, Ibuprohm, Ibu-Tab, Ibutex, Ifen, Medipren, Midol 200, Motrin-IB, Cramp End, Profen, Ro-Profen, Trendar, Alaxan, Brofen, Alfam, Brufen, Algofen, Brufort, Amersol, Bruzon, Andran, Buburone, Anflagen, Butacortelone, Apsifen, Deflem, Artofen, Dolgit, Artril, Dolocyl, Bloom, Donjust, Bluton, Easifon, Ebufac, Emflam, Emodin, Fenbid, Fenspan, Focus, Ibosure, Ibufen, Ibufug, Ibugen, Ibumetin, Ibupirac, Imbun, Inabrin, Inflam, Irfen, Librofen, Limidon, Lopane, Mynosedin, Napacetin, Nobafon, Nobgen, Novogent, Novoprofen, Nurofen, Optifen, Paduden, Paxofen, Perofen, Proartinal, Prontalgin, Q-Profen, Relcofen, Remofen, Roidenin, Seclodin, Tarein, and Zofen), indomethacin (also known as Indameth, Indocin, Amuno, Antalgin, Areumatin, Argilex, Artherexin, Arthrexin, Artrinovo, Bavilon, Bonidon, Boutycin, Chrono-Indocid, Cidalgon, Confortid, Confortind, Domecid, Durametacin, Elemetacin, Idicin, Imbrilon, Inacid, Indacin, Indecin, Indocap, Indocen, Indocid, Indoflex, Indolag, Indolar, Indomed, Indomee, Indometacinum, Indometicina, Indometin, Indovis, Indox, Indozu, Indrenin, Indylon, Inflazon, Inpan, Lauzit, Liometace, Metacen, Metindon, Metocid, Mezolin, Mobilan, Novomethacin, Peralgon, Reflox, Rheumacid, Rheumacin, Salinac, Servindomet, Toshisan, and Vonum), ketoprofen (also known as Orudis, Alrheumat, Alrheumun, Alrhumat, Aneol, Arcental, Dexal, Epatec, Fastum, Keduril, Kefenid, Keprofen, Ketofen, Ketonal, Ketosolan, Kevadon, Mero, Naxal, Oruvail, Profenid, Salient, Tofen, and Treosin), ketorolac (also known as Toradol), meclofenamate (also known as Meclofen, Meclomen, and Movens), mefenamic acid (also known as Ponstel, Alpain, Aprostal, Benostan, Bonabol, Coslan, Dysman, Dyspen, Ecopan, Lysalgo, Manic, Mefac, Mefic, Mefix, Parkemed, Pondex, Ponsfen, Ponstan, Ponstyl, Pontal, Ralgec, and Youfenam), nabumetone (also known as Relafen), naproxen (also known as Naprosyn, Anaprox, Aleve, Apranax, Apronax, Arthrisil, Artrixen, Artroxen, Bonyl, Congex, Danaprox, Diocodal, Dysmenalgit, Femex, Flanax, Flexipen, Floginax, Gibixen, Headlon, Laraflex, Laser, Leniartil, Nafasol, Naixan, Nalyxan, Napoton, Napren, Naprelan, Naprium, Naprius, Naprontag, Naprux, Napxen, Narma, Naxen, Naxid, Novonaprox, Nycopren, Patxen, Prexan, Prodexin, Rahsen, Roxen, Saritilron, Sinartrin, Sinton, Sutony, Synflex, Tohexen, Veradol, Vinsen, and Xenar), oxaprozin (also known as Daypro), piroxicam (also known as Feldene, Algidol, Antiflog, Arpyrox, Atidem, Bestocam, Butacinon, Desinflam, Dixonal, Doblexan, Dolonex, Feline, Felrox, Fuldin, Indene, Infeld, Inflamene, Lampoflex, Larapam, Medoptil, Novopirocam, Osteral, Pilox, Piraldene, Piram, Pirax, Piricam, Pirocam, Pirocaps, Piroxan, Piroxedol, Piroxim, Piton, Posidene, Pyroxy, Reucam, Rexicam, Riacen, Rosic, Sinalgico, Sotilen, Stopen, and Zunden), sulindac (also known as Clinoril, Aflodac, Algocetil, Antribid, Arthridex, Arthrocine, Biflace, Citireuma, Clisundac, Imbaral, Lindak, Lyndak, Mobilin, Reumofil, Sudac, Sulene, Sulic, Sulindal, Suloril, and Sulreuma), tolmetin (also known as Tolectin, Donison, Midocil, Reutol, and Safitex), celecoxib (also known as Celebrex), meloxicam (also known as Mobic), rofecoxib (also known as Vioxx), valdecoxib (also known as Bextra), aspirin (also known as Anacin, Ascriptin, Bayer, Bufferin, Ecotrin, and Excedrin) and steroidal anti-inflammatory drugs including cortisone, prednisone and dexamethasone.

In some embodiments, the first or second bioactive agent is a vasoconstrictor, including, but not limited to, epinephrine (adrenaline, Susphrine), phenylephrine hydrochloride (Neo-Synephrine), oxymetazoline hydrochloride (Afrin), norepinephrine (Levophed), and caffeine.

In some embodiments, the first or second bioactive agent is a vasodilator, including, but not limited to, bosentan (Tracleer), epoprostenol (Flolan), treprostinil (Remodulin), sitaxsentan, nifedipine (Adalat, Procardia), nicardipine (Cardene), verapamil (Calan, Covera-HS, Isoptin, Verelan), diltiazem (Dilacor XR, Diltia XT, Tiamate, Tiazac, Cardizem), isradipine (DynaCirc), nimodipine (Nimotop), amlodipine (Norvasc), felodipine (Plendil), nisoldipine (Sular), bepridil (Vascor), hydralazine (Apresoline), minoxidil (Loniten), isosorbide dinitrate (Dilatrate-SR, Iso-Bid, Isonate, Isorbid, Isordil, Isotrate, Sorbitrate), isorbide mononitrate (IMDUR), prazosin (Minipress), cilostazol (Pletal), treprostinil (Remodulin), cyclandelate, isoxsuprine (Vasodilan), nylidrin (Arlidin), nitrates (Deponit, Minitran, Nitro-Bid, Nitrodisc, Nitro-Dur, Nitrol, Transderm-Nitro), benazepril (Lotensin), benazepril and hydrochlorothiazide (Lotensin HCT), captopril (Capoten), captopril and hydrochlorothiazide (Capozide), enalapril (Vasotec), enalapril and hydrochlorothiazide (Vaseretic), fosinopril (Monopril), lisinopril (Prinivil, Zestril), lisinopril and hydrochlorothiazide (Prinzide, Zestoretic), moexipril (Univasc), moexipril and hydrochlorothiazide (Uniretic), perindopril (Aceon), quinapril (Accupril), quinapril and hydrochlorothiazide (Accuretic), ramipril (Altace), trandolapril (Mavik), papaverine (Cerespan, Genabid, Pavabid, Pavabid HP, Pavacels, Pavacot, Pavagen, Pavarine, Pavased, Pavatine, Pavatym, Paverolan).

In some embodiments, the first or second bioactive agent is a diuretic, including, but not limited to, acetazolamide (Diamox), dichlorphenamide (Daranide), methazolamide (Neptazane), bendroflumethiazide (Naturetin), benzthiazide (Exna), chlorothiazide (Diuril), chlorthalidone (Hygroton), hydrochlorothiazide (Esidrix, HydroDiuril, Microzide), hydroflumethiazide (Diucardin), indapamide (Lozol), methyclothiazide (Enduron), metolazone (Zaroxolyn, Mykrox), polythiazide (Renese), quinethazone (Hydromox), trichlormethiazide (Naqua), bumetanide (Bumex), ethacrynic acid (Edecrin), furosemide (Lasix), torsemide (Demadex), amiloride (Midamor), amiloride and hydrochlorothiazide (Moduretic), spironolactone (Aldactone), spironolactone and hydrochlorothiazide (Aldactazide), triamterene (Dyrenium), triamterene and hydrochlorothiazide (Dyazide, Maxzide).

In some embodiments, the first or second bioactive agent is an anti-cancer agent, including, but not limited to, aldesleukin, alemtuzumab, alitretinoin, allopurinol, altretamine, amifostine, anagrelide, anastrozole, arsenic trioxide, asparaginase, bexarotene, bicalutamide, bleomycin, busulfan, calusterone, capecitabine, carboplatin, carmustine, celecoxib, chlorambucil, cisplatin, cladribine, cyclophosphamide, cytarabine, dacarbazine, dactinomycin, darbepoetin alpha, daunorubicin, daunomycin, dexrazoxane, docetaxel, doxorubicin, epoetin alpha, estramustine, etoposide, etoposide phosphate, exemestane, filgrastim, floxuridine, fludarabine, flutamide, fulvestrant, gemcitabine, gemtuzumab ozogamicin, goserelin acetate, hydroxyurea, ibritumomab tiuxetan, idarubicin, ifosfamide, imatinib mesylate, interferon alpha-2a, interferon alpha-2b, irinotecan, leflunomide, letrozole, leucovorin, levamisole, lomustine, meclorethamine (nitrogen mustard), megestrol acetate, melphalan, mercaptopurine, mesna, methotrexate, methoxsalen, mitomycin C, mitotane, mitoxantrone, mycophenolate mofetil, nandrolone phenpropionate, nilutamide, nofetumomab, oprelvekin, oxaliplatin, paclitaxel, pamidronate, pegademase, pegaspargase, pegfilgrastim, pentostatin, pipobroman, plicamycin, porfimer sodium, procarbazine, quinacrine, rasburicase rituximab, sargramostim, streptozocin, tacrolimus, tamoxifen, temozolomide, teniposide, testolactone, thioguanine, thiotepa, topotecan, toremifene, tositumomab, trastuzumab, tretinoin, uracil mustard, valrubicin, vinblastine, vincristine, vinorelbine, and zoledronate.

In some embodiments, the first or second bioactive agent is an siRNA. The RNAi constructs of the present invention are gene(s) that express RNAs that base pair to form a dsRNA RNA region. The RNAs may be a part of the same molecule or different molecules. In preferred embodiments, the RNAi construct comprises a promoter operably linked to a nucleic acid sequence encoding two complementary sequences separated by a loop sequence. The complementary regions correspond to a target RNA sequence separated by a loop sequence. When the RNAi construct is expressed, the complementary regions of the resulting RNA molecule pair with one another to form a double stranded RNA region. The present invention is not limited to loop sequences of any particular length. In some preferred embodiments, the loop sequences range from about 4 to about 20 nucleotides in length. In more preferred embodiments, the loop sequences are from about 6 to about 12 nucleotides in length. In other preferred embodiments, the dsRNA regions are from about 19 to about 23 in length.

In other embodiments, the dsRNA is formed from RNA transcribed from a vector as two separate stands. In other embodiments, the two strands of DNA used to form the dsRNA may belong to the same or two different duplexes in which they each form with a DNA strand of at least partially complementary sequence. When the dsRNA is thus-produced, the DNA sequence to be transcribed is flanked by two promoters, one controlling the transcription of one of the strands, and the other that of the complementary strand. These two promoters may be identical or different. In some embodiments, a DNA duplex provided at each end with a promoter sequence can directly generate RNAs of defined length, and which can join in pairs to form a dsRNA. See, e.g., U.S. Pat. No. 5,795,715, incorporated herein by reference. RNA duplex formation may be initiated either inside or outside the cell.

It will be recognized that after processing the resulting siRNA can comprise two blunt ends, one blunt end and one end with an overhang, or two ends with overhangs. In some embodiments, the end or ends with overhangs comprise an overhang of either one or two nucleotides. As a non-limiting example, a siRNA of 23 nucleotides in length comprises two 19mers with a two nucleotide overhang at each end. As another non-limiting example, a siRNA of 21 nucleotides in length comprises two 19mers with a single nucleotide overhang at each end. As still another non-limiting example, a siRNA of 22 nucleotides in length comprises two 22mers with no overhangs at either end.

Inhibition is sequence-specific in that nucleotide sequences corresponding to the duplex region of the RNA are targeted for genetic inhibition. RNA molecules containing a nucleotide sequence identical to a portion of the target gene are preferred for inhibition. RNA sequences with insertions, deletions, and single point mutations relative to the target sequence have also been found to be effective for inhibition. Thus, sequence identity may optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript.

There is no upper limit on the length of the dsRNA that can be used. For example, the dsRNA can range from about 21 base pairs (bp) of the gene to the full length of the gene or more. In one embodiment, the dsRNA used in the methods of the present invention is about 1000 bp in length. In another embodiment, the dsRNA is about 500 bp in length. In yet another embodiment, the dsRNA is about 22 bp in length. In some preferred embodiments, the sequences that mediate RNAi are from about 21 to about 23 nucleotides. The isolated iRNAs of the present invention mediate degradation of the target RNA.

The double stranded RNA of the present invention need only be sufficiently similar to natural RNA that it has the ability to mediate RNAi for the target RNA. In one embodiment, the present invention relates to RNA molecules of varying lengths that direct cleavage of specific mRNA to which their sequence corresponds. It is not necessary that there be perfect correspondence of the sequences, but the correspondence must be sufficient to enable the RNA to direct RNAi cleavage of the target mRNA. In a particular embodiment, the RNA molecules of the present invention comprise a 3' hydroxyl group.

In some embodiments, the device of the present invention is a freestanding microsheet of a desired size and shape as described above, preferably comprising a first and second bioactive agents (e.g., antimicrobial silver compounds, antimicrobial gallium compounds, or analgesic compounds). The microsheet may preferably be provided in a desired size and shape by cutting the substrate material to a desired size and shape and peeling the microsheet from the substrate. The microsheet may then be applied to a biological surface such as a wound or a medical surface such as the surface of a medical device such as wound covering. In some embodiments, the microsheet is used to modify a wound dressing or biologic wound dressing that is compatible with functionalization by addition of a matrix material. Examples of commercially available wound dressings that can be modified by addition of a microsheet include, but are not limited to, Biobrane™, gauze, adhesive tape, bandages such as Band-Aids®, and other commercially available wound dressings including but not limited to COMPEEL®, DUODERM™, TAGADERM™, and OPSITE®. In some embodiments, the present invention provides methods for transferring a polymer multilayer to a desired surface, such as soft surface. Such soft surfaces include, but are not limited to, skin, a wound bed, a tissue, artificial tissues including artificial skin tissues such as organotypically cultured skin tissues, Apligraf®, Dermagraft®, Oasis®, Transcyte®, Cryoskin® and Myskin®, artificial tissue matrices, gels comprising biomolecules, a wound dressing, and a biologic wound dressing. In some embodiments, the desired surface is contacted with a polymer multilayer, e.g., a polymer multilayer supported on a support and pressure is applied to effect transfer of the polymer multilayer from the support to the desired surface. In some embodiments, the pressure is from about 10 to about 500 kPa. In some embodiments, the transfer is performed in the substantial, or complete, absence of solution. Such dry transfer processes do not involve exposure of biological components of the desired surface to aqueous solutions containing species that may influence the activity of the biological components. In some embodiments, the transfer is performed through a gas phase. In some embodiments, the transfer is performed in an environment where the humidity is less than 100% of saturation. In some embodiments, the transfer is performed in the absence of liquid water.

Accordingly, in some embodiments, the present invention provides wound dressings comprising a support material having a surface oriented to a wound, wherein the surface oriented to the wound is modified with a microsheet material of the present invention. When applied to a wound, the surface of the support material modified with the matrix material is put into contact with the wound bed.

In some embodiments, the support is a biologic wound dressing. In some embodiments, the biologic wound dressing is a type of wound dressing that comprises, e.g., is coated with or incorporates, cells (e.g., keratinocytes or fibroblasts and combinations thereof) and/or one or more biomolecules or fragments of biomolecules that can be placed in contact with the wound surface. The biomolecules may be provided in the form of an artificial tissue matrix comprising one or more biomolecules. Examples of such biomolecules include, but are not limited, to collagen, glycosaminoglycans, hyaluronic acid, laminin, vitronectin, fibronectin, keratin, antimicrobial polypeptides and combinations thereof. Examples of suitable biologic wound dressings include, but are not limited to, BIOBRANE™, Integra™ Apligraf®, Dermagraft®, Oasis®, Transcyte®, Cryoskin® and Myskin®.

In some embodiments, the microsheets are sued to modify a biosynthetic wound dressing constructed of an elastomeric film (e.g., a silicone film) supported on support material, such as a fabric, preferably a polymeric fabric such as a nylon fabric. In some embodiments, the fabric is at least partially imbedded into the film (e.g., BioBrane™). In some embodiments, the elastomeric film is coated with one or more biomaterials, for example collagen, keratin, fibronectin, vitronectin, laminin and combinations thereof. Accordingly, the fabric presents to the wound bed a complex 3-D structure to which a biomaterial (e.g., collagen) has been bound, preferably chemically bound. In some preferred embodiments, the surface presented to the wound is further modified with a microsheet material as described above. In some preferred embodiments, the microsheet material is a polyelectrolyte membrane comprising a bioactive agent, preferably selected from one or more of silver nanoparticles, elemental silver, and silver containing compounds such as silver sulfadiazine and/or gallium ions and related compounds, and preferably included in the concentration ranges described above. In some embodiments, the microsheet further comprises nanoscale or microscale particles.

In some embodiments, the microsheet is used to modify an adhesive bandage comprising an adhesive portion (such as an adhesive strip) and an absorbent material, preferably treated or coated with a material (i.e., a non-adherent material) to prevent adhesion to the wound or comprising a layer of non-adherent material, such as Teflon®, on the surface of the absorbent pad that will contact the wound. In some embodiments, the support material is an absorbent pad (e.g., a gauze pad or polymer foam) preferably treated or coated with a material (i.e., a non-adherent material) to prevent adhesion to the wound or comprising a layer of non-adherent material, such as Teflon® or other suitable material, on the surface of the absorbent pad that will contact the wound. In some embodiments, the non-adhesive material or layer is breathable. In some embodiments, the wound dressing comprises a gel-forming agent, for example, a hydrocolloid such as sodium carboxymethylcellulose. In some embodiments, the absorbent pads or gel-forming agents are affixed to a material that is waterproof and/or breathable. Examples include, but are not limited, semipermeable polyurethane films. The waterproof and/or breathable material may further comprise an adhesive material for securing the bandage to the skin of a subject. The waterproof and/or breathable material preferably forms the outer surface of the adhesive bandage or pad, i.e., is the surface opposite of the surface comprising the matrix which contacts the wound.

Examples of such adhesive bandages and absorbent pads include, but are not limited to, to adhesive bandages and pads from the Band-Aid® line of wound dressings, adhesive bandages and pads from the Nexcare® line of wound dressings, adhesive bandages and non-adhesive pads from the Kendall Curity Tefla® line of wound dressings, adhesive bandages and pads from the Tegaderm® line of wound dressings, adhesive bandages and pads from the Steri-Strip® line of wound dressings, the COMFEEL® line of wound dressings, adhesive bandages and pads, the Duoderm® line of wound dressings, adhesive bandages and pads, the TEGADERM™ line of wound dressings, adhesive bandages and pads, the OPSITE® line of wound dressings, adhesive bandages and pads, adhesive bandages and pads from the Allevyn™ line of wound dressings, adhesive bandages and pads from the Duoderm® line of wound dressings, and adhesive bandages and pads from the Xeroform® line of wound dressings.

In some embodiments, the devices of the invention are used to modify a medical device such as a surgical mesh. Examples of commercially available surgical meshes that can be modified by addition of a matrix as described below include, but are not limited to, polypropyelene, polyester, polytetrafluoroethylene meshes, or absorbable biomeshes, or biological meshes (biomeshes), including but not limited to ULTRAPRO™ mesh, PROCEED™ mesh, PROLENE™ polypropyelene mesh, Ethicon Physiomesh™ MERSILENE™ polyester mesh, PARIETEX™ mesh, DOLPHIN™ polypropylene mesh, GORE INFINIT™ mesh, PERFIX™, KUGEL™, 3DMAX™, BARD™, VISILEX™, XENMATRIX™, ALLOMAX™, SURGISIS BIODESIGN™, and TIGR MATRIX™.

In some embodiments, a device of the present invention as described above is applied to a wound under conditions such that wound healing, as measured by wound contraction, is accelerated. The devices of the present invention can be applied to all types of wounds. Furthermore, a wound modifying agent with one or more bioactive agents can be applied to skin, mucous membranes, body cavities, and to internal surfaces of bones, tissues, etc. that have been damaged. The devices find use on wounds such as cuts, abrasions, ulcers, surgical incision sites, burns, and to treat other types of tissue damage. In some embodiments of the present invention, the microsheets enhance wound healing. The present invention contemplates that wound healing may be enhanced in a variety of ways. In some embodiments, the compositions and methods minimize contracture of the wound as to best favor function and cosmesis. In some embodiments, compositions and methods promote wound contracture to best favor function and cosmesis. In some embodiments, the compositions and methods promote vascularization. In some embodiments, the compositions and methods inhibit vascularization. In some embodiments, the compositions and methods promote fibrosis. In some embodiments, the compositions and methods inhibit fibrosis. In some embodiments, the compositions and methods promote epithelial coverage. In some embodiments, the compositions and methods inhibit epithelial coverage. In some embodiments, the compositions and methods of the present invention modulates one or properties of cells in the wound environment or in the immediate vicinity of the wound. The properties that are modulated, e.g., are increased or decreased, include, but are not limited to adhesion, migration, proliferation, differentiation, extracellular matrix secretion, phagocytosis, MMP activity, contraction, and combinations thereof. The devices of the present invention can be covered with a secondary dressing, or bandage, if desired to protect the layer or to provide additional moisture absorption, for example.

EXPERIMENTAL

The examples below serve to further illustrate the invention, to provide those of ordinary skill in the art with a complete disclosure and description of how the compounds, compositions, articles, devices, and/or methods claimed herein are made and evaluated, and are not intended to limit the scope of the invention. The examples are not intended to restrict the scope of the invention.

1. INTRODUCTION

Herein we report the design of polymeric constructs formed by the layering of films containing silver nanoparticles (AgNPs) or Bp that allow controlled co-release of both agents, thus minimizing cytotoxicity toward mammalian cells involved in wound healing (fibroblasts). The approach builds from our prior reports of AgNP-loaded films (polyelectrolyte multilayers (PEMs) containing low loadings of silver) that can be placed into conformal contact with wound beds to significantly lower microbial burden while still promoting normal healing of wounds.[4] In addition, we reported that a sacrificial poly(vinyl alcohol) (PVA) microfilm can be deposited over AgNP-PEMs (assembled on a PDMS sheet) and following baking, the PEM/PVA composite can be peeled from the PDMS sheet to form robustly handled microfilms.[4-6] When the PEM/PVA composite is placed onto wounds, the PVA layer dissolves, and leaving the PEMs immobilized on the wound surface.

Herein we report the use of the PVA microfilm not just as a sacrificial layer (to facilitate transfer of the PEM onto the wound) but also as a microscopic reservoir for Bp. We demonstrate that the PEM/PVA microfilm composite containing AgNPs (loaded within a nanoscopically thin (~100 nm) PEM) and Bp (loaded within a micrometer thick (~30-60 μm) PVA film) can serve as a platform to co-deliver $Ag^+$ and Bp (as shown in FIG. 1). In addition, we reveal that an additional film (thickness of ~20-40 μm) of poly(lactic-co-glycolic acid) (PLGA) deposited within the construct can be used to control diffusion of Bp from the Bp-PVA and hence provide a sustained release of BPs. The versatility of the approach is also demonstrated by using a second, thick PLGA barrier layer (thickness of ~120-130 μm) as the topmost layer of the construct to bias the release of the agents toward the wound surface and away from the overlying wound fluid.

The approach described above for achieving unidirectional release of Bp towards the wound surface was tested on murine wound to determine if the construct promoted normal wound healing and to identify doses of Bp that would cause impairment of normal healing of wounds. We also demonstrate the design of a composite film containing both AgNPs and Bp. The construct released doses of Bp and Ag that avoided cytotoxicity toward fibroblasts while simultaneously showing in vitro antibacterial activity. Overall, the study provides guidance to the design of multilayered polymeric constructs that permit control over the rate and direction of release of multiple agents.

2. MATERIALS AND METHODS 2.1 Materials. Poly(allyl amine hydrochloride) PAH (Mw=65 kDa), PVA (Mw=13-23 kDa, 98% hydrolyzed), bupivacaine hydrochloride monohydrate, and PLGA (50:50) (ester terminated; Mw=38-54 kDa) were obtained from Sigma Aldrich (St. Louis, MO). Silver nitrate [$Ag(NO_3)$] was obtained from Alfa Aesar (Ward Hill, MA), and poly (acrylic acid) PAA (Mw=50 kDa) was obtained from Polysciences (Warrington, PA). Polished silicon wafers were purchased from Silicon Sense (Nashua, NH). Reagent grade solvents, standard salts and media were purchased from Sigma Aldrich (Milwaukee, WI) or Fisher Scientific (Pittsburgh, PA) and used without further purification unless otherwise noted. A 6 mm biopsy punch was purchased from Miltex, Inc. (York, PA). *P. aeruginosa* (ATCC 27853) used in biofilm assays was obtained from ATCC (Manassas, VA). 48-well tissue culture plates (#353078) were purchased from Becton, Dickinson, and Company (Franklin Lakes, NJ). Trypticase soy agar with 5% sheep blood was obtained from BD (Sparks, MD).

2.2 Cytotoxicity of solutions of Bp or $Ag^+$ ions. The mouse fibroblast cell line NIH-3T3, obtained from ATCC (Manassas, VA) was used for all in vitro cell-based experiments. Cell cultures were maintained at 37° C. and were fed with DMEM growth medium supplemented with 10% calf bovine serum (CBS), $2\times10^{-3}$ m-glutamine (Invitrogen, Carlsbad, CA), and 1% Penicillin Streptomycin. Cells were seeded with $1.0\times10^4$ cells/well of the 96-well plate and were allowed to attach on the bottom of wells for 24 h. After incubation, cells were washed with 10 μm Phosphate Buffer Saline (PBS); pH 7.4). Next, solutions of Bp or $Ag^+$ ($AgNO_3$) (in 10 μm PBS; pH 7.4) were added to the wells and incubated for an additional 24 h. Cells treated with 1% Triton X-100 (Sigma Aldrich, St Louis, MO) were used as controls for complete cell death. For the evaluation of cytotoxicity, the CellTiter 96 $AQ_{ueous}$ non-radioactive assay (Promega, Germany) was performed. This assay measures the conversion (reduction) of a weakly colored tetrazolium salt of MTS (3-{4,5-dimethylthiazol-2-yl}-5-{3-carboxymethoxyphenyl}-2-{4-sulfophenyl}-2H-tetrazolium) to brightly colored formazan by mitochondrial dehydrogenase of metabolically active (live) cells. The amount of formazan formed varies proportionally with the number of live cells. The wells were rinsed with PBS to remove non-adherent cells and then incubated in a serum-free medium containing 20% MTS reagent for 3 h at 37° C. Then, the absorbance was read in a spectrophotometric plate reader at 490 nm (BioTek Instruments, Winooski, VT).

2.3 Fabrication of PEMs and loading of silver nanoparticles in PEMs. PDMS sheets were fabricated by curing Sylgard184 (Dow Chemical, Midland, MI) on octadecyltrichlorosilane (OTS)-functionalized silicon wafers or glass slides at 60° C. for 24 h (see details elsewhere).[4] Aqueous solutions of polyelectrolytes of PAH and PAA were prepared at 0.01 M (with respect to the molecular weight of the polymer repeat unit). The pH of PAH and PAA solutions were adjusted to 7.5 and 2.5, respectively. To assemble the PEMs, the PDMS sheets were first immersed into a PAH solution for 10 mM followed by three 1 min rinses with deionized water (Millipore, 18.2 MΩ). Next, the substrates were immersed in PAA solution for 10 min followed by the rinsing steps described above. The adsorption and rinsing steps were repeated until the desired number of multilayers was deposited, as described elsewhere.[4]

Incorporation of AgNPs within the PEMs was initiated by incubation of the preassembled PEMs on PDMS in an aqueous solution of $Ag(NO_3)$ (10 mM) at pH ~5-6 for at least 2 h, followed by rinsing in distilled water (pH ~5-6) three times (15 s each) and air drying to form $Ag^+$ within the PEMs. Subsequently, the PEMs were incubated in aqueous $NaBH_4$ (2 mM) solution for 1 mM and again rinsing with water to reduce the $Ag^+$ within PEMs to form $Ag(0)$ nanoparticles. Repeated incubation in $Ag^+$ solutions followed by reducing agent solutions can be used to increase the loading of silver in the PEMs, as described previously.[9,4]

2.4 Fabrication of PVA and PLGA microfilm. To fabricate uniformly thick PVA microfilms containing various loadings of Bp, 25 μL of 2.5% w/v solution of PVA containing various concentrations of Bp (2-20 mg $mL^{-1}$) was spread over a PDMS sheet (diameter 6 mm), and baked at 70° C. for ~10 mM to remove the water. To fabricate PLGA barrier layer, 100 μL of PLGA solution (1%, 1.75%, or 5% w/v dissolved in chloroform) was spread on a PDMS sheet (or over the pre-fabricated structure) and dried at room temperature overnight. Subsequently, the PLGA film was dried under vacuum (at room temperature) to remove excess solvent. The PLGA sheet was subsequently peeled from the PDMS sheet and placed onto a PEM.

2.5 Characterization of loading and release of Bp and Ag with PEM/PVA/PLGA composite films. The loading of silver within PEM/PVA/PLGA composites was determined by extracting the silver from the composite, (punched circles 6 mm in diameter, prepared using a biopsy punch) into 2% nitric acid (5 mL) by incubation for 24 h. The concentration of $Ag^+$ extracted from the composite was measured by elemental analysis using inductively coupled plasma optical emission spectrometry (ICP-OES, Vista-MPX CCD Simultaneous ICP-OES, Varian Inc., CA) at a wavelength of 328.1 nm.[4]

The release of $Ag^+$ from the PEMs into aqueous solution was quantified by ICP. Sample substrates were individually placed into the bottom of 48-well plates, immersed in PBS buffer (1 mL) and incubated without agitation. Substrates were removed daily and placed into new vials containing fresh PBS, with at least three samples prepared per experimental group. For ICP analysis, 1 mL of solution from each vial was combined with 2 mL of 3% nitric acid. The release of Bp (from PVA film) into PBS was determined by measuring the absorbance of Bp within the PBS solution using spectrophotometry (Nanodrop2000, Thermo Scientific (vendor: NanodropTechnologies), Wilmington, DE) at wavelength of 196 nm.

2.6 Antibacterial activity of composite film containing Bp and AgNPs. *P. aeruginosa* (ATCC 27853) was obtained from ATCC (Manassas, VA). Bacteria were grown in Tryptic Soy Broth Yeast Extract (TSBYE) (BD, Franklin Lakes, NJ) overnight at 37° C. with shaking at 200 rpm until a cell density of approximately $4\times10^9$ CFU $mL^{-1}$ was reached. The bacterial suspensions were centrifuged at 4000 rpm for 10 min and the pellet washed and resuspended in PBS buffer. The test samples (supported on PDMS disks) were placed at the bottom of the wells of 48-well plates and the disks were exposed to three fresh 500 μL PBS cultures (pH 7.4) containing $10^7$ CFU of bacteria over a 3-day period: 1st incubation (over 0-24 h), 2nd (24-48 h), 3rd (48-72 h), with the disks transferred to new plates every 24 h (i.e. between each incubation period). The incubation was performed on a shaker (150 rpm) at 37° C. Following each incubation period, the bacteria suspended in the PBS solution were serially diluted in PBS and plated on trypticase soy agar with 5% sheep blood. Bacterial colonies were counted and used to calculate the mean colony forming units (CFU) per mL.

3. RESULTS AND DISCUSSION 3.1 Cytotoxicity of Bp and $Ag^+$ toward fibroblasts. As described in the Introduction, a key goal of our research was to develop a construct that would permit simultaneously delivery of anesthetic and antibacterial agents (Bp and $Ag^+$, respectively) onto wound surfaces without causing cytotoxicity to mammalian cells and/or causing a delay in wound healing. As an initial step towards this goal, we first determined the cytotoxicity limits of Bp and $Ag^+$ using NIH 3T3 mouse fibroblasts. Briefly, fibroblasts were allowed to attach on the bottom of 96-well plates (within 24-h incubation). Subsequently, solutions of Bp or $Ag^+$ ($AgNO_3$) (in 10 μm PBS; pH 7.4) were added to the wells and incubated for an additional 24 h. Following incubation, the viability of the cells was determined by measuring cellular mitochondrial dehydrogenase activity (see Materials and Methods for details). Inspection of FIG. 2a reveals two conclusions. First, the cytotoxicity limit (defined as the concentration of agent that caused a ~50% decrease in viability of cells) was determined to be 1.5 μg mL$^{-1}$ for Ag$^+$ and 1.2 μg mL$^{-1}$ for Bp. Second, Ag$^+$, at concentrations of 0.4 μg mL$^{-1}$ (concentration reported to cause 6 $\log_{10}$ CFU decrease of *P. aeruginosa*) and up to 1.2 μg mL$^{-1}$,[6] was found not to cause significant toxicity toward fibroblasts. Third, Bp, at concentrations typically injected into wound sites for local pain management (1.25-5 mg mL$^{-1}$),[1] cause significant toxicity toward fibroblasts (50-70% decrease in viability of cells). At lower concentrations of Bp (0.2-0.6 mg mL$^{-1}$) however, no significant toxicity of fibroblast was measured.

Figure 6:
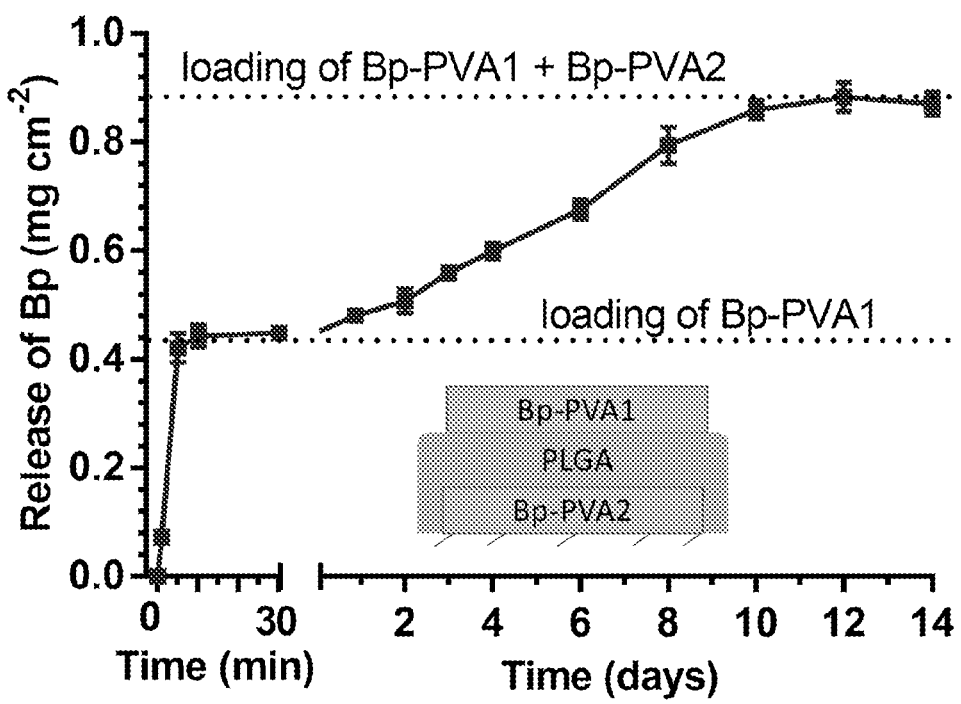
Figure 7:
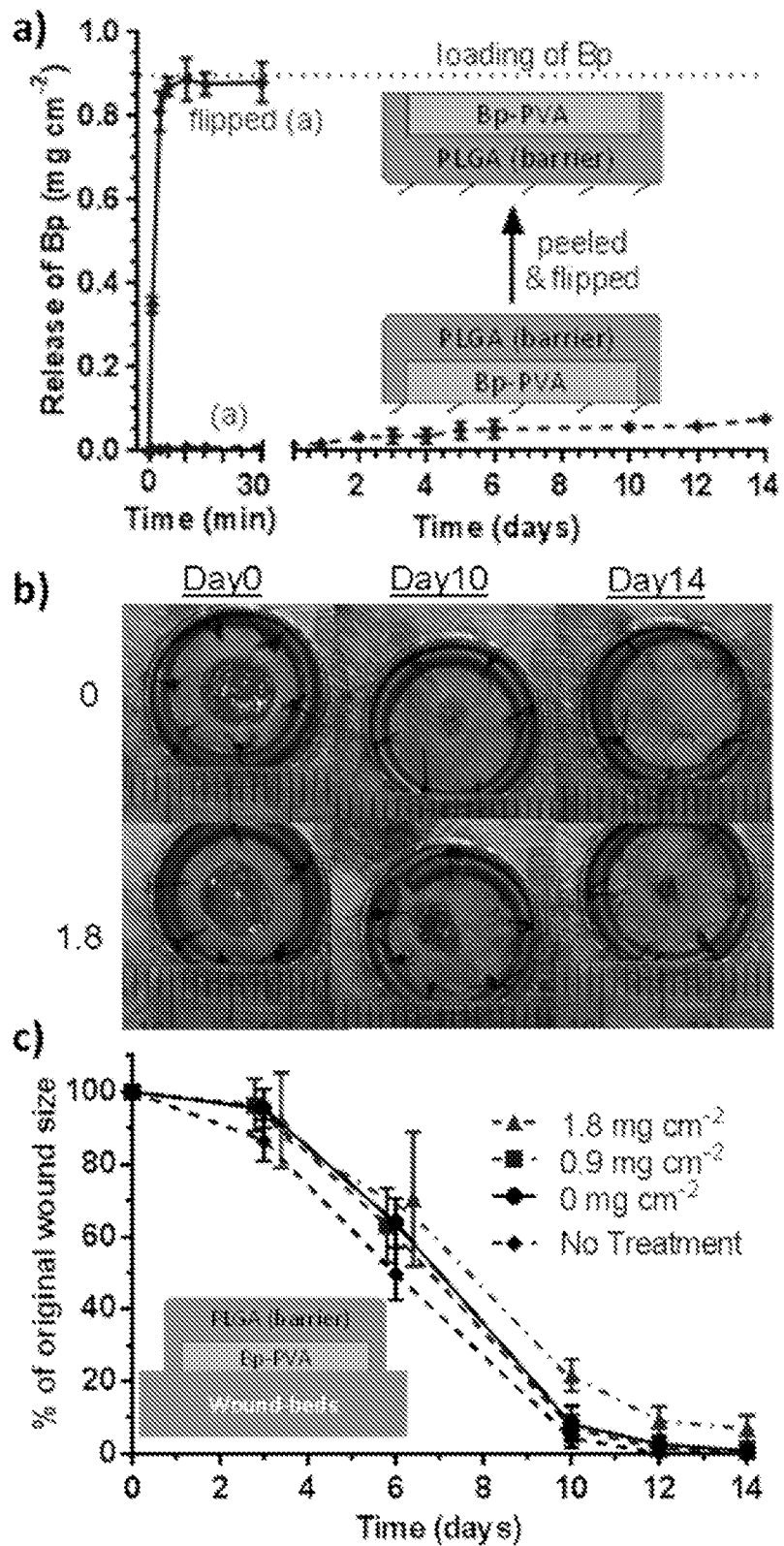
Figure 8:
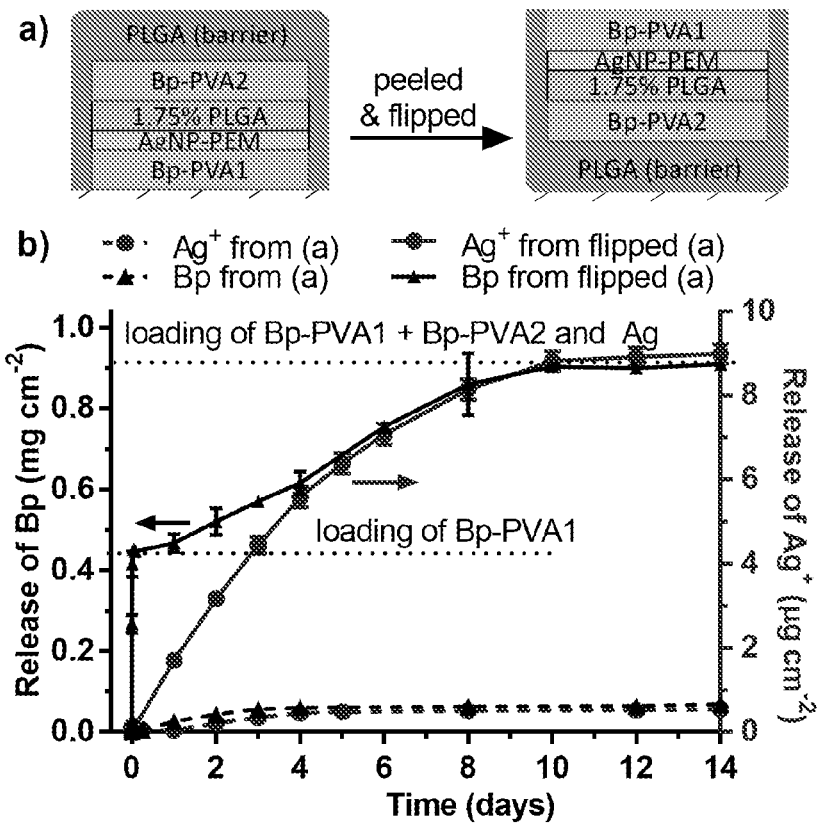
Figure 9:
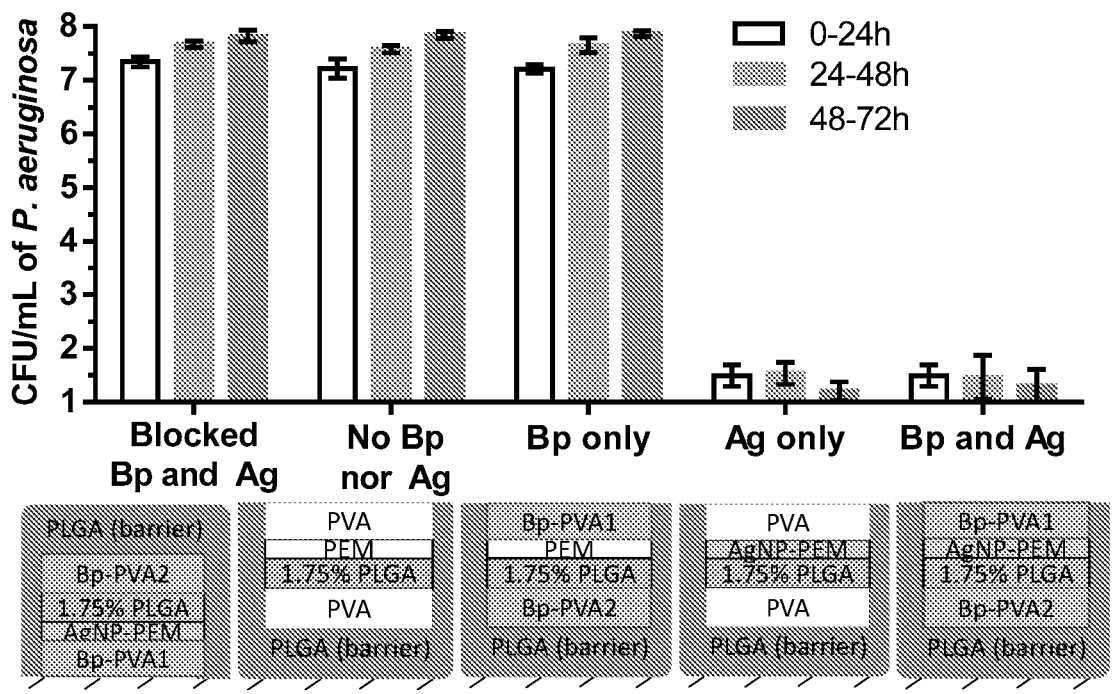

Since Bp (at a concentration of 2.5 mg mL$^{-1}$) has been reported to also exhibit antimicrobial activity,[1] we next determine if Bp, at a lower non-cytotoxic concentration of 0.5 mg mL$^{-1}$, exhibits antimicrobial activity, and when mixed with Ag$^+$, increases antibacterial activity. To explore this issue, a bacteria inoculum ($10^7$ CFU in 500 μL HBSS buffer) containing Bp (0.5 mg mL$^{-1}$) or Ag$^+$ (0.3 or 0.4 μg mL$^{-1}$) or a mixture of Bp and Ag$^+$ was incubated in 48-well plates on shaker plates (150 rpm) at 37° C. for 24 h. Viable bacterial counts remaining in suspension following the 24-h incubation were determined by dilution and plating. FIG. 2b shows that 0.3 and 0.4 μg mL$^{-1}$ of Ag$^+$ was able to cause 3 $\log_{10}$ and 6 $\log_{10}$ CFU decrease of *P. aeruginosa*, respectively. In addition, the figure shows that 0.5 mg mL$^{-1}$ Bp does not exhibit antimicrobial activity and when mixed with Ag$^+$, causes no increase in the antimicrobial activity. Overall, these result suggest that co-delivery of Ag$^+$ (antibacterial agent) and Bp (anesthetic agent) onto a wound surface should generate concentrations of 0.4 μg mL$^{-1}$ Ag$^+$ (or up to 1.2 μg mL$^{-1}$ Ag$^+$) and 0.5 mg mL$^{-1}$ of Bp so that cytotoxicity toward fibroblasts can be avoided (while an antibacterial activity can still be achieved).

3.2 Fabrication of PVA-PLGA microfilm composites containing Bp with controlled loading and release rates. Guided by the above results, we next developed methods aimed at permitting co-delivery of both Bp (0.5 mg $mL^{-1}$ or at lower concentrations) and $Ag^+$ (0.4 μg $mL^{-1}$). Previously, we reported that $Ag^+$ can be loaded into PEMs comprised of PAH and PAA (with thickness of 80-100 nm), and the loaded $Ag^+$ subsequently reduced to form AgNPs to provide a sustained release of $Ag^+$ (see below for details).[9] Because the target release concentrations of Bp (0.6 mg $mL^{-1}$) are 1250× higher than $Ag^+$ (0.4 μg $mL^{-1}$), we loaded Bp into micrometer-thick polymeric film of PVA (rather than into nanometer-thick PEMs).

Our first goal was to control the dose of Bp delivered from the platform and the duration of the release. To fabricate a uniformly thick PVA microfilm containing the desired loadings of Bp, 25 μL of a 2.5% w/v solution of PVA containing Bp (2, 4, 10, 20 mg $mL^{-1}$) was spread over a PDMS sheet (diameter of 6 mm), and baked at 70° C. for ~10 min to remove the water. We characterized the release of Bp (from PVA film) into PBS by measuring the absorbance of Bp within the PBS solution. The loading of Bp determined as the maximum amount of Bp released into solution. FIG. 3*a* shows that by varying the concentration of Bp within PVA solution from 2 to 20 mg $mL^{-1}$, the loading of Bp within the PVA film can be varied from 0.2 to 1.8 mg $cm^{-2}$. Also, we found Bp to be released into the media (as PVA film dissolves) within 5-10 minutes. This result suggests that application of Bp-loaded PVA films onto wound sites would potentially be useful for rapid pain relief following injury. In addition, we note that PVA films with Bp loadings of 0.2, 0.4, 0.9 mg $cm^{-2}$ when released into the 0.5 mL solution within which the films were to be incubated (0.5 mL solution was used for an antimicrobial assay of film containing Bp and Ag, see below), generate concentrations of Bp of 0.1, 0.2, and 0.5 mg $mL^{-1}$, respectively (assuming all Bp is released during the incubation period); these concentrations of Bp were found to be noon-toxic toward fibroblasts. In contrast, Bp loadings of 1.8 mg $cm^{-2}$, when released into the incubated solution, generate Bp concentration of 1 mg $mL^{-1}$, which are toxic toward fibroblasts. To avoid cytotoxicity toward fibroblasts, we used Bp loadings of 0.2 to 0.9 mg $cm^{-2}$ within the PVA film.

Next, we aimed to demonstrate a construct deign that would extend the duration of delivery of Bp from the PVA. Specifically, we coated a Bp-loaded PVA film (Bp loadings of 0.9 mg $cm^{-2}$) with a barrier layer of biodegradable PLGA film (copolymer of 50% poly-lactic acid and 50% of polyglycolic acid). We aimed to achieve continuous delivery of Bp over the time that it takes for a typical wound to heal (10-14 days). Various concentrations of PLGA (1%, 1.75%, or 5% w/v dissolved in chloroform) were used to systematically vary the thickness of the barrier layer (100 μL PLGA solution was used to create PLGA films with diameter of 8 mm). As shown in FIG. 3*b*, capping of the Bp-PVA film with PLGA extended the release rate of Bp from minutes to days. Also, varying the thickness of PLGA layer changed the release rate of the Bp. Specifically, PLGA films that were made from 1% and 1.75% PLGA solution (with thickness of 20-25 μm, 35-40 μm, respectively) provided 90% release of Bp within 3 days and 10 days, respectively, while the thickest PLGA film (with thickness of 120-130 μm; made from 5% PLGA solution) released only 10% of Bp within 14 days. This result suggests that a PLGA cap made from 1.75% PLGA solution can be used to provide a continuous delivery of Bp over the time it typically takes for wounds to heal (10-14 days).

3.3. Providing a burst release of Bp followed by a sustained release over 14 days. Our second goal was to design and fabricate embodiments of the delivery platform that provided a burst release of Bp, followed by a sustained release of Bp over 14 days. Our approach to achieve such a release profile involved the synthesis of a laminated microfilm structure consisting of (i) a Bp-loaded PVA film, (ii) a PLGA film, and (iii) a second Bp-loaded PVA film (order of layering is listed from top to bottom layer). The two bottom layers of the structure (i.e. PLGA capped Bp-PVA film) were fabricated with the method described above. Subsequently, we spread PVA solution (containing Bp) over the PLGA layer to create the topmost layer of Bp-PVA film. We loaded 0.45 mg $cm^{-2}$ in each PVA film separated by the PLGA film (i.e. made from 1.75% PLGA solution) to give the total loadings of 0.9 mg $cm^{-2}$. The release profile of this structure is shown in FIG. 4. The figure shows that the structure provided a burst release of Bp (within minutes; from the top most Bp-PVA film) followed by a sustained release of Bp (within days; from the bottom layers containing 1.75% PLGA cap). Such a release profile of Bp would be potentially useful for achieving rapid pain relief on wounds following injury, followed by continuous pain relief during healing.

3.4 Unidirectional release of Bp from PVA-PLGA composite toward wound surface and its affect in wound healing. Our third goal was to optimize the delivery platform to achieve directional release of Bp into wound surface, thus minimizing loss of Bp released into the overlying wound fluid. We also aimed to determine if treatment of wounds with the Bp-loaded structures impair the normal healing of the wounds. Since a PLGA cap (made from 5% solution), when overlying a Bp-loaded PVA film, provided an efficient barrier against diffusion of Bp from the underlying PVA layer (as shown above), we used an overlying thick PLGA layer aimed to direct the release of the Bp toward the bottom side of the layered structure. When the layered structure was peeled from PDMS and subsequently placed on the wound surface, we hypothesize that the active agents within the delivery platform will be released in the direction of the wound surface.

To test this hypothesis, we fabricated a structure that consisted of a Bp-PVA layer that was topped with a thick PLGA film (made from 5% PLGA) over a PDMS sheet (see section 3.2 for fabrication method). This PVA-PLGA composite was easily peeled from the PDMS sheet to form free-standing film. The release of Bp from the bottom side of the structure was characterized by flipping the structure (Bp-PVA layer as the top layer). FIG. 5*a* shows the release profile (both upward and downward release) of the structure that was loaded with 0.9 mg $cm^{-2}$ of Bp. As shown in FIG. 5*a*, the upward release of Bp was effectively blocked by the presence of the cap layer for up to 14 days. In contrast, a burst release of Bp (within minutes) occurred from the bottom side (as characterized from the flipped structure).

Next, we studied the effect of Bp release (Bp directed onto wound surface and released within minutes, as described above) on the healing of wounds of mice (initial wound size: ~6 mm). We aim to determine if Bp treatment impairs normal healing of wounds. The loadings of Bp within the construct was either 0.9 or 1.8 mg $cm^{-2}$ (6 mice and 7 mice, respectively). As control groups, we used 2 mice whose wounds that were left untreated as well as 7 mice whose wounds were treated with constructs containing no Bp. Wounds were covered with a plastic cover slip placed over splints and the entire construct was covered with Tegaderm (3M). Mice were monitored daily and wounds were photographed on days 0, 3, 6, 10, 12, and 14 after surgery (see images of the representative wounds treated with film containing no Bp or with film containing 1.8 mg $cm^{-2}$ on FIG. 5*b*). These wound photographs were then analyzed to measure sizes of wounds over the period of 14 days (see FIG. 5*c* for results).

FIG. 5*c* shows that, similar to untreated wounds, wounds treated with of PVA/PLGA film containing no Bp (as well as wounds treated with films containing 0.9 mg $cm^{-2}$ Bp) exhibited 93±2% healing on day 10 and complete wound closure on day 14. In contrast, wounds treated with 1.8 mg $cm^{-2}$ Bp only exhibited 78±1% healing on day 10 and were not completely healed (i.e. 93±2% healed) by day 14. A t-test analysis was performed (using PRISM software) to determine the statistical significance of test-treatment on wound size at each time point. It was determined that at any time point, % of healing of untreated wounds and wounds treated with 0.9 mg $cm^{-2}$ Bp (of film containing no Bp) was not significantly different ($p>0.05$). However, % of healing of wounds treated with 1.8 mg $cm^{-2}$ Bp and wounds treated with films containing no Bp (on day 10, 12, and 14) was significantly different ($p<0.01$). Overall, these results shows that treatment of wounds with films loaded with 1.8 mg $cm^{-2}$ Bp impairs normal healing of wounds while wound treatment of 0.9 mg cm 2 Bp does not, indicating that dose of treatment of Bp needs to be carefully controlled (below 1.8 mg $cm^{-2}$) so that normal healing is not impaired.

3.5 Unidirectional release of multiple agents (Bp and $Ag^+$) to achieve antimicrobial activity. Our fourth goal was to integrate an antimicrobial agent (i.e. AgNPs) into the delivery platform containing Bp such that unidirectional and continuous release of both Bp and Ag onto the wound surface would kill bacteria; the release of Bp from the construct was designed such that it provided a burst release followed by a sustained release of Bp. Our approach involved the synthesis of AgNPs-loaded PEMs (as we previously reported),[9,4] and subsequent lamination of the PEMs with microfilms of Bp-PVA and PLGA (with two PVA layers separated by a thin PLGA layer (to provide burst and sustained release of Bp) as well as a thick PLGA layer as the topmost layer (to direct release of Bp and $Ag^+$ toward the bottom side of the structure); see FIG. 6*a* for the lamination layers leading to the multi-agent construct).

We fabricated the above-mentioned structure via a four-step fabrication process. First, we synthesized PEMs via layer-by-layer assembly of PAH and PAA on PDMS sheet and loaded the PEMs with AgNPs (see Materials and Methods and below for the specific loadings of silver). Second, we laminated the nanofilm with a Bp-PVA microfilm by spreading a PVA solution containing Bp over the PEM. Following baking, the PEM/PVA composite was peeled from the PDMS sheet and subsequently flipped, thus orienting the Bp-PVA as the bottom most layer. Third, we deposited a 1.75% PLGA microfilm on top of the AgNP-PEMs. To avoid direct contact of the chloroform solvent (containing PLGA) with the AgNP-PEMs (if the PLGA solution is pipetted directly over the PEMs, it will cause deposition of PLGA within the PEM and hence block release of Ag ions from the PEMs), we pursued the following strategy for fabrication: we pre-fabricated the PLGA microfilm on a separate PDMS sheet, and then transfer the pre-fabricated PLGA microfilm onto the nanofilm (peeling the PDMS used to back the PLGA microfilm). Fourth, we spread PVA solution containing Bp over the PLGA layer, and subsequently (following drying of the PVA solution) cap the structure with 5% PLGA layer (capping with 5% PLGA was described in section 3.2).

Since $Ag^+$ ions (at concentrations of 0.4 μg $mL^{-1}$ or as much as 1 μg $mL^{-1}$) do not induce significant cytotoxicity to fibroblasts, but still provide antibacterial activity, we fabricated the above described composite film to contain 10 μg $cm^{-2}$ of silver. This loading of silver was guided by our previous report that a similar loading of AgNPs-PEMs released $Ag^+$ in a sustained manner to reduce microbial burden without causing impairment of normal healing of mice wounds. The physical processes that controls the loading of AgNPs into PEMs has been described in detail in previous reports. To achieve the loading of 10 μg $cm^{-2}$ of silver within PEMs (as described above), we fabricated 10 bilayers of PEMs that were made of PAH (pH 7.5) and PAA (pH2.5) and then performed three silver ion exchange and reduction cycles (as described above). Also, in order to avoid cytotoxicity toward fibroblasts, we load each of the two PVA layers within the composite film with 0.45 mg $cm^{-2}$ Bp, giving the total Bp loadings of 0.9 mg $cm^{-2}$. Specifically, we calculated that the maximum release of Bp from the composite (all Bp within the composite is released) would generate concentrations of 0.5 mg $mL^{-1}$ Bp (when released into 0.5 mL solution within which the PEMs were to be incubated) that are non-toxic toward fibroblasts. In addition, use of 0.9 mg $cm^{-2}$ Bp (when applied on mice wounds) cause no impairment of normal healing of mice wounds (see above).

We next characterized the release of both Bp and Ag from the composite film. Release of agents from the bottom and top side of the film were characterized from the flipped and non-flipped structure, respectively. Bp release was characterized using spectrophotometry while $Ag^+$ release was characterized using elemental analysis (see Materials and Methods for details), and the results are shown in FIG. 6b. The figure shows that both $Ag^+$ ions and Bp was released from the bottom side of the film (flipped film) while both agents were largely blocked from release from the top side of the film (only 7-8% of agents were released on day 14; due to PLGA barrier). Specifically, the composite provided a daily release (from the bottom side of film) of 0.7-1.7 µg $cm^{-2}$ of $Ag^+$ for 6 days and 0.4 µg $cm^{-2}$ thereafter (from the AgNPs-PEMs). Also, 0.45 mg $cm^{-2}$ of Bp was released from the bottom side of the film within minutes (from the bottom most PVA layer) followed a sustained release of Bp (within days; due to the presence of 1.75% PLGA film underneath the second PVA layer).

Next, we tested the effectiveness of the composite film for killing bacteria. In brief, we sequentially exposed the composite film that contains both AgNPs and Bp (flipped film) to three fresh cultures of bacteria of *P. aeruginosa* over a 3 day period (see Materials and Methods for details). Non-flipped film and flipped film containing AgNPs or Bp alone were used as controls. FIG. 7 shows the antibacterial results. As shown in FIG. 7, we measured (from the bottom side of the composite film) the release of Bp alone to exhibit no antibacterial activity while the release of $Ag^+$ (released alone or when co-released with Bp) was effective in exhibiting antibacterial activity (causing 6 $log_{10}$ CPU decrease of *P. aeruginosa*) for all three successive 24*h* inoculations. The figure also shows that the non-flipped film exhibited no antibacterial activity. These results indicate that the release of agents (i.e. $Ag^+$) was successfully blocked from the top side of the film while the continuous release of $Ag^+$ (as well as Bp) from the bottom side of the film can kill bacteria over the period of (at least) 3 days. Hence, this composite film can be potentially applied on wounds (following peeling from PDMS sheet) such that Ag and Bp can be directed onto the wound surface to reduce bacterial burden while also achieving pain relieve. We note that when released into the 0.5 mL of solution in which the PDMS was incubated, the above-described composite film (d=6 mm) generated $Ag^+$ and Bp, at concentrations of 1.7 μg $mL^{-1}$ and 0.25 mg $mL^{-1}$, respectively, after each incubation period of 24 h. We emphasize that these concentrations do not significantly reduce the viability of mammalian cells important for wound healing, such as fibroblasts.

4. CONCLUSION

This study demonstrates an approach to the fabrication of polymeric nanofilm/microfilm composites containing multiple agents (one agent within the nanofilm (PEM) and the other agent within the microfilm) that permit control of the dose and rate of delivery of multiple agents. Using AgNPs and the anesthetic agent of Bp as model agents incorporated within the PEMs and microfilm of PVA, respectively, we showed that the approach (i) permits precise loadings of both agents, (ii) allows incorporation of a PLGA film (as a sealant) within the composite film to alter the release profile of the agents from the film (i.e. to direct release of agents toward wound surface), (iii) can provide co-release of both $Ag^+$ and Bp from the surface of film to exert antibacterial activity toward *P. aeruginosa* without inducing toxicity to fibroblasts, and (iv) can be used to functionalize wound surfaces while still promoting normal healing of wounds. An additional merit of the approach is that it can be potentially used to release other pain-relieving agents from the PVA microfilm (i.e. lidocaine,[7] ketamine,[8] tramadol, etc) as well as other bioactive agents that have been incorporated into the PEMs (including peptides, proteins, DNA, and small organic molecules).

REFERENCES (1) Johnson, S. M.; Saint John, B. E.; Dine, A. P. Local Anesthetics as Antimicrobial Agents: A Review. *Surg. Infect.* (*Larchmt*). 2008, 9 (2), 205-213.

(2) Dere, K.; Sen, H.; Teksoz, E.; Ozkan, S.; Dagli, G.; Sucullu, I.; Filiz, A. I.; Ipcioglu, O. M.; Kucukodaci, Z. The Comparison of the Effects of Different Doses of Levobupivacaine Infiltration on Wound Healing. *J. Invest. Surg. Off. J. Acad. Surg. Res.* 2009, 22 (2), 112-116.

(3) Hanci, V.; Hakimo, S.; Özaçmak, H.; Bekta, S.; Özaçmak, H. S.; O, S.; Yurtlu, S.; Turan, Ö. Comparison of the Effects of Bupivacaine, Lidocaine, and Tramadol Infiltration on Wound Healing in Rats. R*ev. Bras. Anestesiol.* 2012, 62 (6), 799-810.

(4) Herron, M.; Agarwal, A.; Kierski, P. R.; Calderon, D. F.; Teixeira, L. B. C.; Schurr, M. J.; Murphy, C. J.; Czuprynski, C. J.; McAnulty, J. F.; Abbott, N. L. Reduction in Wound Bioburden Using a Silver-Loaded Dissolvable Microfilm Construct. *Adv. Healthc. Mater.* 2014, 3, 916-928.

(5) Herron, M.; Schurr, M. J.; Murphy, C. J.; McAnulty, J. F.; Czuprynski, C. J.; Abbott, N. L. Gallium-Loaded Dissolvable Microfilm Constructs That Provide Sustained Release of Ga3+ for Management of Biofilms *Adv. Healthc. Mater.* 2015, 4, 2849-2859.

(6) Herron, M.; Schurr, M. J.; Murphy, C. J.; McAnulty, J. F.; Czuprynski, C. J.; Abbott, N. L. Interfacial Stacks of Polymeric Nanofilms on Soft Biological Surfaces That Release Multiple Agents. *ACS Appl. Mater. Interfaces* 2016, 8 (40), 26541-26551.

(7) Cai, X. Y.; Xiong, L. M.; Yang, S. H.; Shao, Z. W.; Xie, M.; Gao, F.; Ding, F. Comparison of Toxicity Effects of Ropivacaine, Bupivacaine, and Lidocaine on Rabbit Intervertebral Disc Cells in Vitro. *Spine J.* 2014, 14 (3), 483-490.

(8) Haas, D. A.; Harper, D. G. Ketmine: A Review of Its Pharmacologic Use in Ambulatory Anesthesia Properties and Use in Ambulatory Anesthesia. *Anesth. Prog.* 1992, 39, 61-68.

(9) Agarwal, A.; Weis, T. L.; Schurr, M. J.; Faith, N. G.; Czuprynski, C. J.; McAnulty, J. F.; Murphy, C. J.; Abbott, N. L. Surfaces Modified with Nanometer-Thick Silver-Impregnated Polymeric Films That Kill Bacteria but Support Growth of Mammalian Cells. *Biomaterials* 2010, 31, 680-690.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

What is claimed is:

1. A method of treating a wound comprising applying a device to the surface of wound, the device comprising:

a first polymer layer comprising a first bioactive agent, wherein the first polymer layer is a nanoscale polymer multilayer comprising alternating layers of at least one positively charged polyelectrolyte and at least one negatively charged polyelectrolyte;

a second polymer layer comprising a second bioactive agent, wherein the second polymer layer is a water soluble microscale polymer layer; and a third polymer layer positioned in between the first and second polymer layers so that the three polymer layers are stacked in a sandwich-type structure, wherein the third polymer layer is a water soluble microscale polymer layer formed from a different polymer than the second polymer layer.

2. The method of claim 1, wherein the at least one positively charged polyelectrolyte is selected form the group consisting of poly (allylamine hydrochloride) (PAH), polyllysine (PLL), poly (ethylene imine) (PEI), poly (histidine), poly (N,N-dimethyl aminoacrylate), poly (N,N,N-trimethylaminoacrylate chloride), poly (methyacrylamidopropyltrimethyl ammonium chloride), and natural polysaccharides.

3. The method of claim 1, wherein said at least one negatively charged polyelectrolyte is selected from the group consisting of poly (acrylic acid) (PAA), poly (styrenesulfonate) (PSS), alginate, hyaluronic acid, heparin, heparan sulfate, chondroitin sulfate, dextran sulfate, poly (methacrylic acid), oxidized cellulose, carboxymethyl cellulose, polyaspartic acid, and polyglutamic acid.

4. The method of claim 1, wherein the first bioactive agent is an antimicrobial agent selected from the groups consisting of small molecule antimicrobial agents, charged small molecule antimicrobial agents, antimicrobial polypeptides, metallic particles, and bioactive metal ions.

5. The method of claim 1, wherein the first bioactive agent is a silver ion, silver salt, or silver nanoparticle.

6. The method of claim 1, wherein the first bioactive agent is a gallium ion, gallium salt, or gallium nanoparticle.

7. The method of claim 1, wherein the second polymer layer is selected from the group consisting of polyvinyl alcohol (PVA), polyacrylic acid (PAA), polyvinylpyrrolidone (PVP), carboxymethyl cellulose (CMC), sodium carboxymethyl cellulose, methylcellulose, ethylcellulose, ethylmethyl cellulose, hydroxyethyl cellulose (HEC), hydroxylpropyl cellulose (HPC), hydroxypropyl methylcellulose (HPMC), alginates, polyvinylacetate (PVAc), polylactic acid (PLA), polylactic-co-glycolic acid (PLGA), polyglycolic acid, and polyanhydrides.

8. The method of claim 1, wherein the second bioactive agent is an analgesic agent selected from the group consisting of acetaminophen, anileridine, acetylsalicylic acid, buprenorphine, butorphanol, fentanyl, fentanyl citrate, codeine, rofecoxib, hydrocodone, hydromorphone, hydromorphone hydrochloride, levorphanol, alfentanil hydrochloride, meperidine, meperidine hydrochloride, methadone, morphine, nalbuphine, opium, levomethadyl, hyaluronate sodium, sufentanil citrate, capsaicin, tramadol, leflunomide, oxycodone, oxymorphone, celecoxib, pentazocine, propoxyphene, benzocaine, lidocaine, dezocine, clonidine, butalbital, phenobarbital, tetracaine, phenazopyridine, sulfamethoxazole/phenazopyridine, sulfisoxazole/phenazopyridine, amylocaine, ambucaine, articaine, benzocaine, benzonatate, bupivacaine, butacaine, butanilicaine, chloroprocaine, cinchocaine, cyclomehtycaine, dibucaine, diperodon, dimethisoquin, dimethocaine, eucaine, etidocaine, hexylcaine, fomocaine, fotocaine, hydroxyprocaine, isobucaine, levobupivicaine, iodocaine, mepivacaine, meprylcaine, metabutoxycaine, nitracaine, orthocaine, oxetacaine, oxybuprocaine, paraethocycaine, phenacaine, piperocaine, piridocaine, pramocaine, prilocaine, primacaine, procaine, procainamide, proparacaine, propoxycaine, pyrrocaine, quinisocaine, ropivacaine, trimecaine, tetracaine, tolycaine, and tropacocaine.

9. The method of claim 1, wherein the analgesic agent is a local anesthetic selected from the group consisting of bupivacaine, lidocaine, articaine, prilocaine, and mepivacaine.

10. The method of claim 1, wherein the third polymer layer is selected from the group consisting of polyvinyl alcohol (PVA), polyacrylic acid (PAA), polyvinylpyrrolidone (PVP), carboxymethyl cellulose (CMC), sodium carboxymethyl cellulose, methylcellulose, ethylcellulose, ethylmethyl cellulose, hydroxyethyl cellulose (HEC), hydroxylpropyl cellulose (HPC), hydroxypropyl methylcellulose (HPMC), alginates, polyvinylacetate (PVAc), polylactic acid (PLA), polylactic-co-glycolic acid (PLGA), polyglycolic acid, and polyanhydrides.

11. The method of claim 1, wherein the third polymer layer is PLGA.

12. The method of claim 1, wherein the third polymer layer modulates diffusion of the second bioactive agent towards a wound bed when the device is applied to a wound.

13. The method of claim 1, wherein the third polymer layer has a thickness of from 10 to 100 μm.

14. The method of claim 13, further comprising a fourth polymer layer positioned beneath the first polymer layer in the sandwich-type structure, the fourth polymer layer comprising an analgesic agent.

15. The method of claim 14, further comprising a fifth polymer layer positioned above the second polymer layer in the sandwich-type structure.

* * * * *